United States Patent
Papeer et al.

(10) Patent No.: US 10,395,881 B2
(45) Date of Patent: Aug. 27, 2019

(54) SYSTEMS AND METHODS FOR PROVIDING AN ION BEAM

(71) Applicant: HIL Applied Medical, Ltd., Jerusalem (IL)

(72) Inventors: Evgeny Papeer, Jerusalem (IL); Assaf Shaham, Haifa (IL); Shmuel Eisenmann, Seattle, WA (US); Yair Ferber, Jerusalem (IL); Ynon Hefets, Jerusalem (IL); Omer Shavit, Jerusalem (IL); Boaz Weinfeld, Jerusalem (IL); Sagi Brink-Danan, Jerusalem (IL)

(73) Assignee: HIL APPLIED MEDICAL, LTD., Jerusalem (IL)

( * ) Notice: Subject to any disclaimer, the term of this patent is extended or adjusted under 35 U.S.C. 154(b) by 0 days.

(21) Appl. No.: 15/730,255

(22) Filed: Oct. 11, 2017

(65) Prior Publication Data
US 2019/0108965 A1 Apr. 11, 2019

(51) Int. Cl.
*H01J 27/24* (2006.01)
*H01J 27/02* (2006.01)
(Continued)

(52) U.S. Cl.
CPC ............... *H01J 27/24* (2013.01); *A61N 5/10* (2013.01); *H01J 27/022* (2013.01); *H05H 15/00* (2013.01); *A61N 2005/1088* (2013.01)

(58) Field of Classification Search
CPC ......... H05H 15/00; H01J 27/24; H01J 27/022
See application file for complete search history.

(56) References Cited

U.S. PATENT DOCUMENTS

| 4,264,815 A | 4/1981 | Reuter |
| 4,870,287 A | 9/1989 | Cole et al. |

(Continued)

FOREIGN PATENT DOCUMENTS

| EP | 1232516 | 8/2002 |
| EP | 2795656 | 10/2014 |
| EP | 3014629 | 5/2016 |

OTHER PUBLICATIONS

K. D. Xiao et al.; "Enhanced Target Normal Sheath Acceleration of Protons From Intense Laser Interaction with a Cone-Tube Target", AIP Advances, vol. 6, pp. 015303-1 to 015303-8 (2016).

(Continued)

*Primary Examiner* — Wyatt A Stoffa
(74) *Attorney, Agent, or Firm* — Finnegan, Henderson, Farabow, Garrett & Dunner, LLP

(57) ABSTRACT

Systems for generating a proton beam include an electromagnetic radiation beam (e.g., a laser) that is directed onto an ion-generating target by optics to form the proton beam. A detector is configured to measure a laser-target interaction property, which a processor uses to produce a feedback signal that can be used to alter the proton beam by adjusting the source of the electromagnetic radiation beam, the optics, or a relative position or orientation of the electromagnetic radiation beam to the ion-generating target. By adjusting the laser-target interaction, the feedback can be used to control properties of the proton beam, such as the proton beam energy or flux. Such systems have certain advantages, including reducing the size, complexity, and cost of machines used to generate proton beams, while also improving their speed, precision, and configurability.

18 Claims, 15 Drawing Sheets

(51) Int. Cl.
*A61N 5/10* (2006.01)
*H05H 15/00* (2006.01)

(56) References Cited

U.S. PATENT DOCUMENTS

| | | | |
|---|---|---|---|
| 5,037,602 A | 8/1991 | Dabiri et al. | |
| 5,760,395 A | 6/1998 | Johnstone | |
| 5,825,845 A | 10/1998 | Blair et al. | |
| 5,854,710 A | 12/1998 | Rao et al. | |
| 6,473,062 B1 | 10/2002 | Debiez et al. | |
| 6,683,318 B1 | 1/2004 | Harberer et al. | |
| 6,780,149 B1 | 8/2004 | Schulte | |
| 6,867,419 B2 | 3/2005 | Tajima | |
| 6,906,338 B2 | 6/2005 | Tajima | |
| 6,987,279 B2 | 1/2006 | Hoshino et al. | |
| 7,030,398 B2 | 4/2006 | Tajima et al. | |
| 7,164,144 B2 | 1/2007 | Partlo et al. | |
| 7,189,976 B2 | 3/2007 | Takahashi et al. | |
| 7,268,358 B2 | 9/2007 | Ma et al. | |
| 7,317,192 B2 | 1/2008 | Ma et al. | |
| 7,348,569 B2* | 3/2008 | Feurer | G21K 1/00 |
| | | | 250/400 |
| 7,368,740 B2 | 5/2008 | Beloussov et al. | |
| 7,460,228 B2* | 12/2008 | Takahashi | G21K 1/06 |
| | | | 356/326 |
| 7,555,102 B1 | 6/2009 | Renard-Le Galloudec et al. | |
| 7,570,741 B2 | 8/2009 | Melnychuk et al. | |
| 7,587,024 B2 | 9/2009 | Grozinger et al. | |
| 7,642,521 B2 | 1/2010 | Willi et al. | |
| 7,755,068 B2 | 7/2010 | Ma et al. | |
| 7,782,914 B2 | 7/2010 | Faure et al. | |
| 7,813,476 B2 | 10/2010 | Oosting | |
| 8,222,617 B2* | 7/2012 | Iseki | A61N 5/1043 |
| | | | 250/396 ML |
| 8,229,075 B2 | 7/2012 | Cowan et al. | |
| 8,264,174 B2* | 9/2012 | Liu | H05H 15/00 |
| | | | 250/396 R |
| 8,269,189 B2* | 9/2012 | Ma | H05H 15/00 |
| | | | 250/398 |
| 8,389,954 B2* | 3/2013 | Zigler | G21G 1/10 |
| | | | 250/423 P |
| 8,405,044 B2 | 3/2013 | MacKinnon et al. | |
| 8,530,852 B2* | 9/2013 | Le Galloudec | H01J 27/24 |
| | | | 250/423 P |
| 8,750,459 B2 | 6/2014 | Cowan et al. | |
| 8,796,614 B2 | 8/2014 | Song et al. | |
| 8,872,140 B2 | 10/2014 | Jung et al. | |
| 8,878,464 B2 | 11/2014 | Clayton et al. | |
| 8,948,341 B2 | 2/2015 | Beckman | |
| 9,084,885 B2 | 7/2015 | Deisseroth et al. | |
| 9,108,050 B2 | 8/2015 | Bula et al. | |
| 9,155,185 B2 | 10/2015 | Reijonen et al. | |
| 9,236,215 B2 | 1/2016 | Zigler et al. | |
| 9,329,462 B2 | 5/2016 | Matteo et al. | |
| 9,345,119 B2 | 5/2016 | Adams et al. | |
| 9,390,824 B2 | 7/2016 | Hofmann | |
| 9,468,777 B2 | 10/2016 | Fallone et al. | |
| 9,511,242 B2 | 12/2016 | Uhlemann | |
| 9,530,605 B2* | 12/2016 | Nahum | G21B 3/006 |
| 9,550,075 B2 | 1/2017 | Matteo et al. | |
| 9,586,058 B2 | 3/2017 | Bert et al. | |
| 9,607,377 B2 | 3/2017 | Lovberg et al. | |
| 9,659,736 B2 | 5/2017 | Rosenthal | |
| 9,711,319 B2* | 7/2017 | Zigler | H01J 27/24 |
| 9,764,163 B2 | 9/2017 | Benner et al. | |
| 9,782,606 B2 | 10/2017 | Park et al. | |
| 9,789,342 B2 | 10/2017 | Bach et al. | |
| 9,937,360 B1* | 4/2018 | Papeer | A61N 5/1081 |
| 10,039,935 B1 | 8/2018 | Papeer et al. | |
| 10,049,778 B2 | 8/2018 | Toshiki et al. | |
| 2002/0090194 A1* | 7/2002 | Tajima | G21K 1/003 |
| | | | 385/147 |
| 2004/0013820 A1* | 1/2004 | Cadieu | C23C 14/221 |
| | | | 427/596 |
| 2005/0167610 A1 | 8/2005 | Tajima | |
| 2007/0002336 A1 | 1/2007 | Pellemans et al. | |
| 2007/0242705 A1* | 10/2007 | Faure | H05H 15/00 |
| | | | 372/5 |
| 2008/0089460 A1 | 4/2008 | Sved | |
| 2009/0230318 A1* | 9/2009 | Fourkal | G21B 1/19 |
| | | | 250/423 R |
| 2010/0127183 A1* | 5/2010 | Iseki | A61N 5/1043 |
| | | | 250/396 ML |
| 2011/0047469 A1 | 2/2011 | Baumann et al. | |
| 2011/0098522 A1 | 4/2011 | Drees et al. | |
| 2011/0139997 A1 | 6/2011 | Sakaki et al. | |
| 2011/0248181 A1* | 10/2011 | Zigler | G21G 1/10 |
| | | | 250/423 P |
| 2011/0273115 A1* | 11/2011 | Liu | H05H 15/00 |
| | | | 315/500 |
| 2012/0083645 A1 | 4/2012 | Sun et al. | |
| 2012/0211668 A1* | 8/2012 | Okamura | A61N 5/10 |
| | | | 250/396 R |
| 2012/0223246 A1 | 9/2012 | Stephani et al. | |
| 2013/0153783 A1* | 6/2013 | Zigler | H01J 27/24 |
| | | | 250/423 P |
| 2013/0221234 A1* | 8/2013 | Kakutani | H01J 27/24 |
| | | | 250/423 P |
| 2014/0037062 A1 | 2/2014 | Elgort et al. | |
| 2015/0094838 A1 | 4/2015 | MacLaverty | |
| 2015/0216029 A1 | 7/2015 | Tsuchida | |
| 2015/0272677 A1* | 10/2015 | Jung | A61B 18/22 |
| | | | 606/10 |
| 2016/0059039 A1 | 3/2016 | Liu | |
| 2016/0126052 A1* | 5/2016 | Zigler | H01J 27/24 |
| | | | 250/424 |

OTHER PUBLICATIONS

J. Psikal et al.; "Hollow Target for Efficient Generation of Fast Ions by Ultrashort Laser Pulses", Physics of Plasmas, vol. 23, pp. 123121-1 to 123121-6 (2016).
S. Steinke et al.; "Multistage Coupling of Independent Laser-Plasma Accelerators", Letter Research, Nature, 9 pages (2016).
Prashant Kumar Singh et al.; "Contrasting Levels of Absorption of Intense Femtosecond Laser Pulses by Solids", Scientific Reports, Nature, vol. 5, No. 17870, pp. 1-7 (2015).
F. Wagner et al.; "Maximum Proton Energy above 85 MeV from the Relativistic Interaction of Laser Pulses with Micrometer Thick CH2 Targets", Physical Review Letters, vol. 116, pp. 205002-1 to 205002-5 (2016).
Sergei Tochitsky et al.; "Summary Report of Working Group 6: Laser-Plasma Acceleration of Ions", Advanced Accelerator Concepts, API Conference Proceedings, vol. 1507, pp. 231-239 (2012).
Andrea Macchi; "Ion acceleration by superintense laser-plasma interaction", Reviews of Modern Physics, vol. 85, pp. 751-793 (2013).
Ken W. D. Ledingham et al.; "Towards Laser Driven Hadron Cancer Radiotherapy: A Review of Progress", Applied Sciences, vol. 4, pp. 402-443 (2014).
Hiroyuki Daido et al.; "Review of Laser-Driven Ion Sources and their Applications", Reports on Progress in Physics, vol. 75, pp, 1-71 (2012).
Marco Borghesi; "Laser-Driven Ion Acceleration: State of the Art and Emerging Mechanisms", Nuclear Instruments and Methods in Physics Research A, vol. 740, pp. 6-9 (2014).
J. Schreiber et al.; "Invited Review Article: "Hands-on" Laser-Driven Ion Acceleration: A Primer for Laser-Driven Source Development and Potential Applications", Review of Scientific Instruments, vol. 87, pp. 071101-1 to 071101-10 (2016).
Ute Linz et al.; "Laser-Driven Ion Accelerators for Tumor Therapy Revisited", Physical Review Accelerators and Beams, vol. 19, pp. 124802-1 to 124802-8 (2016).
Malka et al., Principles and Applications of Compact Laser-Plasma Accelerations, Nature Physics, vol. 4, at pp. 447-453 (Jun. 2008).
Ledingham et al., Towards a Laser Driver Hadron Cancer Radiotherapy: A Review of Progress, Applied Sciences, vol. 4(3), at pp. 402-443 (Sep. 2014).

(56) References Cited

OTHER PUBLICATIONS

Macchi et al., Ion Acceleration by Superintense Laser-Plasma Interaction, Reviews of Modern Physics, vol. 85, at pp. 751-793 (May 2013).
K. D. Xiao et al.; "Enhanced Target Normal Sheath Acceleration of Protons From Intense Laser Interaction with a Cone-Tube Target", AIP Advances, vol. 6, pp. 015303-1 to 015303-8 (Jan. 7, 2016).
J. Psikal et al.; "Hollow Target for Efficient Generation of Fast Ions by Ultrashort Laser Pulses", Physics of Plasmas, vol. 23, pp. 123121-1 to 123121-6 (Dec. 28, 2016).
C. Scullion et al.; "Polarization Dependence of Bulk Ion Acceleration from Ultrathin Foils Irradiated by High-Intensity Ultrashort Laser Pulses", Physical Review Letters, vol. 119, pp. 054801-1 to 054801-6 (Aug. 2, 2017).
S. Steinke et al.; "Multistage Coupling of Independent Laser-Plasma Accelerators", Letter Research, Nature, 9 pages (Feb. 1, 2016).
Prashant Kumar Singh et al.; "Contrasting Levels of Absorption of Intense Femtosecond Laser Pulses by Solids", Scientific Reports, Nature, vol. 5, No. 17870, pp. 1-7 (Dec. 9, 2015).
F. Wagner et al.; "Maximum Proton Energy above 85 MeV from the Relativistic Interaction of Laser Pulses with Micrometer Thick CH2 Targets", Physical Review Letters, vol. 116, pp. 205002-1 to 205002-5 (May 19, 2016).
Hannes Pahl; "Exploring the Use of Graphene as a Target Material for Laser Plasma Ion Acceleration", Lund Reports on Atomic Physics, vol. 533, 59 pages (Jan. 31, 2017).
Özgür Culfa; "Measurements of Proton Energy Spectra Generated by Ultra Intense Laser Solid Interactions", Journal of Natural and Applied Sciences, pp. 1-7 (Jun. 6, 2017).
Reza Fazeli; "Study of the Laser-Plasma Acceleration of Ion Beams with Enhanced Quality: The Effects of Nanostructured Targets", Journal of Applied Physics, vol. 121, pp. 223301-1 to 223301-7 (Jun. 9, 2017).
Lieselotte Obst et al.; "Efficient Laser-Driven Proton Acceleration from Cylindrical and Planar Cryogenic Hydrogen Jets", Scientific Reports, vol. 7, No. 10248, pp. 1-9 (Aug. 31, 2017).
Deep Kumar Kuri et al.; "Proton Acceleration from Magnetized Overdense Plasmas", Physics of Plasmas, vol. 24, pp. 013112-1 to 013112-7 (Jan. 18, 2017).
S. Souri et al.; "Laser-Driven Proton Acceleration Enhancement by the Optimized Intense Short Laser Pulse Shape", Physics of Plasmas, vol. 24, pp. 053108-1 to 053108-7 (May 19, 2017).
A. Yogo et al.; "Boosting Laser-Ion Acceleration with Multi-Picosecond Pulses", Scientific Reports, vol. 7, No. 42451, pp. 1-10 (Feb. 13, 2017).
Andrea Lübcke et al.; "Prospects of Target Nanostructuring for Laser Proton Acceleration", Scientific Reports, vol. 7, No. 44030, pp. 1-8 (Mar. 14, 2017).
Juan C. Fernández et al.; "Laser-Plasmas in the Relativistic-Transparency Regime: Science and Applications", Physics of Plasmas, vol. 24, pp. 056702-1 to 05670219 (May 30, 2017).
Sergei Tochitsky et al.; "Summary Report of Working Group 6: Laser-Plasma Acceleration of Ions," API Conference Proceedings, vol. 1507, pp. 231-239 (Dec. 21, 2012).
Andrea Macchi; "Ion acceleration by superintense laser-plasma interaction", Reviews of Modern Physics, vol. 85, pp. 751-793 (May 10, 2013).
Ken W. D. Ledingham et al.; "Towards Laser Driven Hadron Cancer Radiotherapy: A Review of Progress", Applied Sciences, vol. 4, pp. 402-443 (Sep. 19, 2014).
Hiroyuki Daido et al.; "Review of Laser-Driven Ion Sources and their Applications", Reports on Progress in Physics, vol. 75, pp. 1-71 (Apr. 17, 2012).
S. S. Bulanov et al.; "Summary Report of Working Group 6: Laser-Plasma Acceleration of Ions", Advanced Accelerator Concepts, API Conference Proceedings, vol. 1812, pp. 030006-1 to 030006-9 (Mar. 6, 2017).
Marco Borghesi; "Laser-Driven Ion Acceleration: State of the Art and Emerging Mechanisms", Nuclear Instruments and Methods in Physics Research A, vol. 740, pp. 6-9 (Dec. 26, 2013).
J. Schreiber et al.; "Invited Review Article: "Hands-on" Laser-Driven Ion Acceleration: A Primer for Laser-Driven Source Development and Potential Applications", Review of Scientific Instruments, vol. 87, pp. 071101-1 to 071101-10 (Jul. 28, 2016).
Ute Linz et al.; "Laser-Driven Ion Accelerators for Tumor Therapy Revisited", Physical Review Accelerators and Beams, vol. 19, pp. 124802-1 to 124802-8 (Dec. 29, 2016).
International Search Report and Written Opinion for PCT/US 17/56121, dated Aug. 6, 2018 (17 pages).
Bolton et al., "Instrumentation for diagnostics and control of laser-accelerated proton (ion) beams," Physics Media, Oct. 5, 2013 (16 pages).
Brenner et al., "Dependence of laser accelerated protons on laser energy following the interaction of defocused, intense laser pulses with ultra-thin targets," Laser and Particle Beams, 2011. (7 pages).
Macchi, "Ion acceleration by superintense laser-plasma interaction," arXiv, Feb. 8, 2013 (58 pages).

* cited by examiner

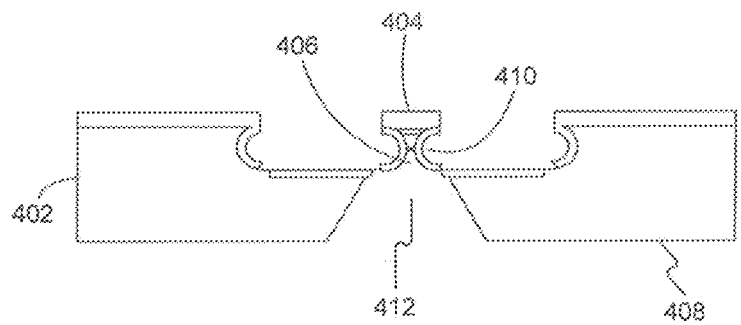
*Fig. 4A*
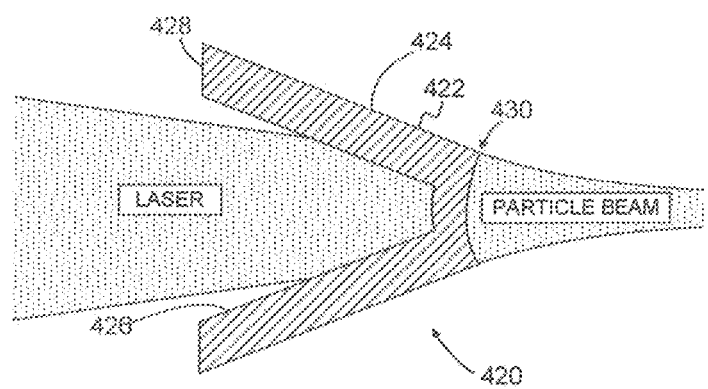
*Fig. 4B*
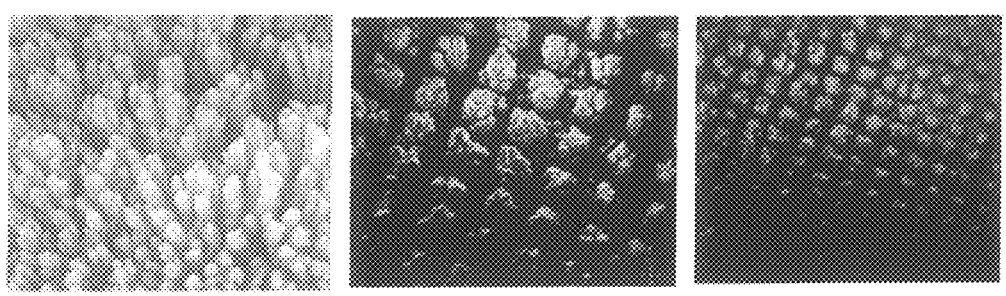
*Fig. 4C*  *Fig. 4D*  *Fig. 4E*

SYSTEMS AND METHODS FOR PROVIDING AN ION BEAM

The disclosed embodiments generally relate to improvements in ion beam generation, including proton beam generation, and particularly to ion beam generation via interactions between an electromagnetic radiation beam and an ion-generating target.

BACKGROUND

Aspects of this disclosure include many systems, subsystems, components and subcomponents. Background details already known are not repeated herein. Such background information may include information contained in the following materials:
- U.S. Pat. No. 8,229,075 to Cowan et al., titled "Targets and Processes for Fabricating Same," issued Jul. 24, 2012;
- U.S. Pat. No. 8,389,954 to Zigler et al., titled "System for Fast Ions Generation and a Method Thereof," issued Mar. 5, 2013;
- U.S. Pat. No. 8,530,852 to Le Galloudec, titled "Micro-Cone Targets for Producing High Energy and Low Divergence Particle Beams," issued Sep. 10, 2013;
- U.S. Pat. No. 8,750,459 to Cowan et al., titled "Targets and Processes for Fabricating Same," issued Jun. 10, 2014;
- U.S. Pat. No. 9,236,215 to Zigler et al., titled "System for Fast Ions Generation and a Method Thereof," issued Jan. 12, 2016;
- U.S. Pat. No. 9,345,119 to Adams et al., titled "Targets and Processes for Fabricating Same," issued May 17, 2016; and
- U.S. Pat. No. 9,530,605 to Nahum et al., titled "Laser Activated Magnetic Field Manipulation of Laser Driven Ion Beams," issued Dec. 27, 2016.

Particle radio-therapy conducted with ions may be used to treat disease. In one form of particle therapy, called proton therapy, a tumor is treated by irradiating it with protons (e.g., hydrogen ions). Proton therapy has advantages over conventional photon-based therapies (e.g., x-ray and gamma ray therapies) in part due to the way protons and photons interact with a patient's tissue.

FIG. 1 shows the radiation dose as a function of tissue depth for both photon and proton therapies. Before a particle can irradiate the treatment volume 106 defined by the patient's treatment plan, it typically must traverse the patient's skin and other healthy tissue before reaching the treatment volume 106 of the patient. In doing so, the particles can damage healthy tissue, an undesirable side-effect of the treatment. As shown in curve 102 of FIG. 1, photons (e.g., x-rays) deliver most of their energy to the regions near the patient's skin. For tumors deeper in the patient's body, this interaction may damage healthy tissue. Additionally, some photons traverse the patient's body beyond the treatment volume 106, irradiating yet more healthy tissue behind the tumor before ultimately exiting the other side of the patient's body. Although the radiation doses to these other healthy tissues is lower than the dose delivered near the patient's skin, it is still undesirable.

Unlike photons, protons, exhibit a very desirable interaction with the patient's tissue. As shown by curve 104 in FIG. 1, the peak interaction of protons with the patient's tissue occurs deeper within the patient and may cease abruptly after the peak interaction. Additionally, protons interact with surface tissues much less than photons, meaning that the majority of the proton beam's energy can be delivered to the treatment volume 106, and the irradiation of healthy tissue can be reduced. Taking advantage of these benefits, proton therapy thus allows more precise administration of energy to unhealthy tissue in patients while avoiding damage to healthy tissue. For example, proton therapy may reduce damage to surrounding healthy tissue by 2 to 6 times when compared to x-ray therapy, thereby improving patient survival and quality of life. Protons may reduce the lifetime risk of secondary cancer in children by 97%, compared to x-rays.

Commercial proton therapy centers are currently rare due to disadvantages in existing proton therapy systems, which generate proton beams by using large and costly particle accelerators. Accelerator-based systems can be massive and are not scalable. As an example, FIG. 2 shows an approximate size comparison of an accelerator-based proton therapy system against a football field. The energy requirements and maintenance costs inherent in operating an accelerator-based system are also immense. Taken together, these disadvantages lead to exorbitant construction and maintenance costs associated with proton therapy. In addition to the extravagant costs associated with accelerator-based proton beam generation, adjusting certain properties of the proton beam (e.g., the beam energy and beam flux) can be cumbersome and time-consuming in such systems. This leads to longer treatment times and low patient throughput, further increasing the cost of individual treatments as fewer patients share the cost burden. Accordingly, few proton therapy centers currently exist, and patients often receive inferior treatments due, in part, to unavailability of proton therapy.

The present disclosure is directed to alternative approaches to proton therapy. Although the embodiments disclosed herein contemplate the medical application of proton beam therapy, a person of ordinary skill in the art would understand that the novel proton beam generating methods and systems described below can be used in any application where a proton beam is desired.

BRIEF SUMMARY OF EXEMPLARY DISCLOSED EMBODIMENTS

Some of the embodiments disclosed herein provide methods and systems for improved generation of a proton beam. For example, disclosed embodiments may improve upon disadvantages of some conventional proton generation technologies, as described above, for example by providing improved speed, precision, and configurability, allowing proton beam generation to be performed more efficiently and at a lower cost. Disclosed embodiments may further reduce the size and complexity of existing systems.

Consistent with the present embodiments, a system for generating a proton beam may include an interaction chamber configured to support an ion-generating target; an electromagnetic radiation source configured to provide an electromagnetic radiation beam; one or more optics components configured to direct the electromagnetic radiation beam at the ion-generating target to thereby cause a resultant proton beam; a detector configured to measure at least one laser-target interaction property; and at least one processors configured to produce a feedback signal based on the at least one laser-target interaction property measured by the detector and to alter the proton beam by adjusting at least one of the electromagnetic radiation source, the one or more optics component, and at least one of a relative position and orientation of the electromagnetic radiation beam to the ion-generating target.

Some embodiments may include a method including providing an electromagnetic radiation beam; directing the electromagnetic radiation beam at an ion-generating target within an interaction chamber to thereby cause a resultant proton beam; measuring at least one laser-target interaction property; and producing a feedback signal based on the at least one measured laser-target interaction property to alter the proton beam by adjusting at least one of an electromagnetic radiation source, one or more optics component, and at least one of a relative position and orientation of the electromagnetic radiation beam to the ion-generating target.

By way of example, the at least one laser-target interaction property may include a proton beam property (e.g., a proton beam energy or a proton beam flux).

A laser-target interaction property may include a secondary electron emission property, such as, for example, an x-ray emission property.

The electromagnetic radiation source may be configured to provide one or more of a laser beam or, for example, a pulsed electromagnetic radiation beam, for causing a pulsed proton beam.

The interaction chamber may include a target stage for supporting the ion-generating target, and the at least one processor may be further configured to cause relative movement between the target stage and the electromagnetic radiation beam.

A structure of the ion-generating target may be determined, at least in part, for example, based upon a generated feedback signal generated from a measured laser-target interaction property.

Further, consistent with the present embodiments, the at least one laser-target interaction property may include a proton beam energy.

Further, consistent with the present embodiments, the at least one laser-target interaction property may include a proton beam flux.

Further, consistent with the present embodiments, the electromagnetic radiation source may be configured to alter a temporal profile of the electromagnetic radiation beam in response to the feedback signal.

Further, consistent with the present embodiments, the electromagnetic radiation source may be configured to generate at least a main pulse and a pre-pulse, and the at least one processor may be configured to cause the electromagnetic radiation source to alter a contrast ratio of the pre-pulse to the main pulse in response to the feedback signal.

Further, consistent with the present embodiments, at least one processor may be configured to cause the electromagnetic radiation source to alter an energy of the electromagnetic radiation beam in response to the feedback signal.

Further, consistent with the present embodiments, the one or more processors may be configured to cause the electromagnetic radiation source to alter a spatial profile of the electromagnetic radiation beam, for example by altering a spot size of the electromagnetic radiation beam, in response to the feedback signal.

Further, consistent with the present embodiments, the at least one processor may be configured to cause the one or more optics components to alter a spatial profile of the electromagnetic radiation beam, for example by altering a spot size of the electromagnetic radiation beam in response to the feedback signal.

Further, consistent with the present embodiments, the at least one processor may be configured to cause a motor to alter the relative orientation between the electromagnetic radiation beam and the ion-generating target in response to the feedback signal.

Another embodiment consistent with the present disclosures may comprise a system for generating a proton beam, the system comprising an interaction chamber configured to support an ion-generating target; an electromagnetic radiation source configured to provide an electromagnetic radiation beam; an adaptive mirror configured to direct the electromagnetic radiation beam at the ion-generating target in the interaction chamber to thereby generate a proton beam; and at least one processor configured to control the adaptive mirror so as to adjust at least one of a spatial profile of the electromagnetic radiation beam and at least one of a relative position and orientation between the electromagnetic radiation beam and the ion-generating target.

Some embodiments may include a method including providing an electromagnetic radiation beam; directing the electromagnetic radiation beam, using an adaptive mirror, at an ion-generating target within an interaction chamber to thereby cause a resultant proton beam; controlling the adaptive mirror with at least one processor so as to adjust at least one of a spatial profile of the electromagnetic radiation beam and at least one of a relative position and orientation between the electromagnetic radiation beam and the ion-generating target.

By way of example, the adaptive mirror may be configured to direct the electromagnetic radiation beam by at least one of adjusting a focus of the electromagnetic radiation beam, diverting the electromagnetic radiation beam, and scanning the electromagnetic radiation beam.

Further, consistent with the present embodiments, the adaptive mirror may be configured to raster the electromagnetic radiation beam over the ion-generating target.

Further, consistent with the present embodiments, the adaptive mirror may comprise a plurality of facets, each of the plurality of facets being independently controllable by digital logic circuitry.

Further, consistent with the present embodiments, the adaptive mirror may comprise a laser pulse focused onto an anti-reflective coated substrate, one or both of the laser pulse and anti-reflective coated substrate being controllable by a digital logic circuitry.

Further, consistent with the present embodiments, the at least one processor may be configured to cause the adaptive mirror to direct the electromagnetic radiation beam at the ion-generating target in response to a feedback signal.

Further, consistent with the present embodiments, the at least one processor may be configured to cause the adaptive mirror to direct the electromagnetic radiation beam at predetermined locations on a surface of the ion-generating target.

Further, consistent with the present embodiments, a surface of the ion-generating target may include a patterned array.

Further, consistent with the present embodiments, a surface of the ion-generating target may include a plurality of ion-generating structures substantially oriented along a common axis.

Further, consistent with the present embodiments, a surface of the ion-generating target may include at least one knife edge.

Consistent with other disclosed embodiments, non-transitory computer-readable storage media may store program instructions, which are executed by one or more processor devices and perform any of the methods described herein.

The foregoing general description is a brief summary of only a few disclosed embodiments, and is not intended to be restrictive of the numerous inventive concepts set forth in the following drawings, detailed description, and claims.

BRIEF DESCRIPTION OF THE DRAWINGS

The accompanying drawings, which are incorporated in and constitute a part of this specification, illustrate certain aspects of the disclosed embodiments and, together with the description, explain the disclosed embodiments. In the drawings:

FIGS. 4A, 4B, 4C, 4D, and 4E are examples of ion-generating targets for proton beam generation, consistent with disclosed embodiments.

DETAILED DESCRIPTION

Figure 1:
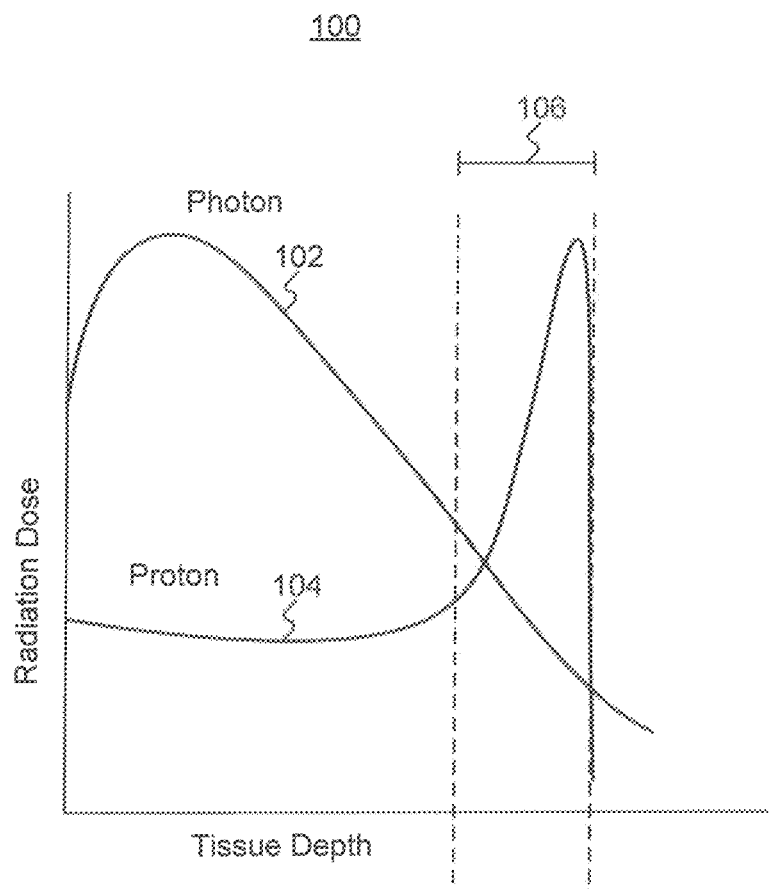
FIG. 1 is a graph depicting radiation dose correlated to tissue depth.
Figure 2:
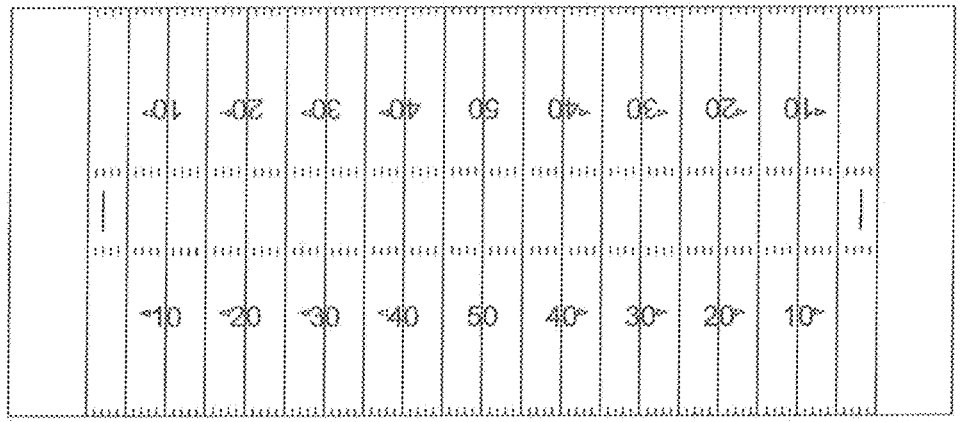
FIG. 2 is an approximate representation of size of some conventional accelerator-based particle therapy systems, as described above.
Figure 2:
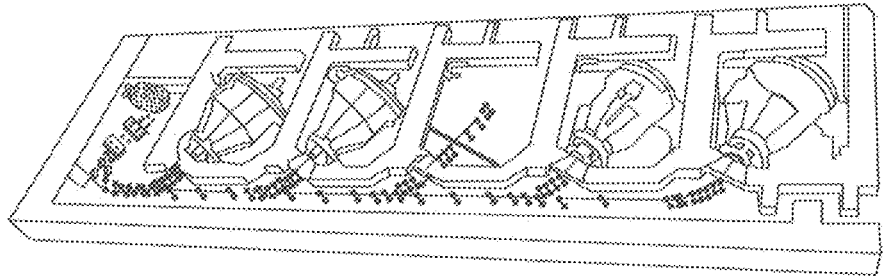

Reference is now made in detail to exemplary embodiments, examples of which are illustrated in the accompanying drawings and disclosed herein. Wherever convenient, the same reference numbers are used throughout the drawings to refer to the same or like parts.

Systems and methods are provided herein for providing ion beam therapy. The following embodiments are described in relation to proton therapy. As used here, "proton therapy" refers to a particle therapy medical procedure that uses a beam of protons to irradiate diseased tissue, most often in the treatment of cancer. While this description refers to this therapeutic procedure, it is to be understood that the intended scope of the innovations herein are not limited to therapy or medical procedures. Rather, it may apply any time a proton beam is generated for any purpose. In addition, the disclosure is not limited to the generation of beams of protons, but also applies to other forms of ion beam generation.

A system for generating a proton beam in accordance with the present disclosure may comprise one or more sources of electromagnetic radiation. "Electromagnetic radiation," as used in the present disclosure may refer to any form of electromagnetic radiation having any wavelength, frequency, energy, power, polarization, and/or spatial or temporal profile. In some embodiments, electromagnetic radiation may propagate in the form of a beam. For example, an electromagnetic radiation beam may be any form of electromagnetic radiation suitable for irradiating a desired location. In some embodiments, a system for providing proton therapy system may be configured to provide an electromagnetic radiation beam along a trajectory. An electromagnetic radiation beam may, for example, be configured for irradiating a plurality of patterned features on an ion-generating target (as described in further detail below) or for irradiating one or more knife edges on an ion-generating target (also described in further detail below).

An electromagnetic radiation beam may comprise a defined energy, wavelength, power, energy, polarization (or it may not be polarized), spatial profile, and/or temporal profile. Any of these traits may be fixed or may vary. As an example, an electromagnetic radiation source may be configured to provide a laser beam having traits tailored to properties of an ion-generating target. An electromagnetic radiation beam may be pulsed, to thereby cause a pulsed proton beam, or it may be continuous to thereby cause a continuous proton beam.

A system for generating a proton beam in accordance with the present disclosure may comprise an ion-generating target. As used in the present disclosure, an ion-generating target may refer to any material, apparatus, or combination of elements configured for generating ions in response to electromagnetic irradiation. As described below, an ion-generating target may be configured for generating a proton beam; however, a proton beam is merely an example. In some embodiments, an ion-generating target may be provided with a plurality of patterned features. For example, a plurality of patterned features may comprise protrusions extending from a surface of an ion-generating target. In some embodiments, an ion-generating target may patterned with one or more knife edges. For example, a knife edge of an ion-generating target may include one or more narrow edges, similar to an arête or the edge of a blade.

A system for generating a proton beam in accordance with the present disclosure may comprise optics component(s). As used in the present disclosure, optics component(s) may refer to any one or more components for manipulating and/or controlling an electromagnetic radiation beam in any manner, including, for example, shaping, directing, filtering, splitting, delaying, modulating, absorbing, amplifying, focusing, chopping, and/or reflecting an electromagnetic radiation beam. As an example, optics components may be positioned along a trajectory of an electromagnetic radiation beam, for example between an electromagnetic radiation source and a surface of an ion-generating target. In some embodiments, optics components may be configured to direct the electromagnetic radiation beam at the ion-generating target, for example to thereby cause a resultant proton beam. Further, an electromagnetic radiation source may include one or more optics components to facilitate formation of an electromagnetic radiation beam.

Consistent with the present disclosure, optics components may include one or more adaptive mirror(s). As used in the present disclosure, an adaptive mirror may refer to an element that includes a reflective surface that may be adapted. For example, an adaptive mirror may be a deformable mirror that comprises a plurality of facets, each of the plurality of facets being independently controllable by a digital logic circuitry. As another example, an adaptive mirror may be a plasma mirror that comprises a laser pulse focused onto an anti-reflective coated substrate, one or both of the laser pulse and anti-reflective coated substrate being controllable by a digital logic circuitry. In some embodiments, an adaptive mirror may be configured to direct an electromagnetic radiation beam at an ion-generating target or, in some instances, configured to cooperate with an electromagnetic radiation beam to cause electromagnetic radiation beam to irradiate the ion-generating target, thereby facilitating formation of a proton beam. An adaptive mirror in accordance with the present disclosure may be configured to adjust or control a spatial profile of an electromagnetic radiation beam and/or to adjust or control at least one of a relative position and orientation between an electromagnetic beam and an ion-generating target. In some instances, an adaptive mirror may be configured to direct an electromagnetic radiation beam by adjusting one or more property of the electromagnetic radiation beam. For example, adjustment may be achieved by at least one of adjusting a focus of the electromagnetic radiation beam, diverting the electromagnetic radiation beam, and scanning the electromagnetic radiation beam.

Consistent with the present disclosure, a system for generating a proton beam may be configured to raster an electromagnetic radiation beam, for example over an ion-generating target. As used in the present disclosure, rastering may refer to a pattern of sequential scanning over a surface or volume having any shape. Rastering may, for example, be achieved by one or more motor configured to cause an electromagnetic radiation beam to sequentially scan a surface or volume. In some embodiments, an electromagnetic radiation beam may be rastered over individual patterned features of an ion-generating target or a knife edge of an ion-generating target. In some embodiments, an adaptive mirror may be configured to direct an electromagnetic radiation beam to strike individual features of an ion-generating target.

A system for generating a proton beam in accordance with the present disclosure may comprise proton beam adjustment component(s). As used in the present disclosure, proton beam adjustment component(s) may refer to any one or more components for manipulating and/or controlling a proton beam in any manner, including, for example, accelerating, analyzing, directing, shaping, filtering, splitting, delaying, modulating, absorbing, amplifying, focusing, chopping, and/or reflecting a proton beam. For example, a proton beam adjustment component may include one or more quadrupole lens, cylindrical mirror lens/analyzer ("CMA"), spherical mirror lens/analyzer ("SMA"), collimator, energy degrader, time-of flight control unit, magnetic dipole, or any other component suitable for manipulating charged ions.

A system for generating a proton beam in accordance with the present disclosure may be used in conjunction with a system for treating a treatment volume with protons. In the case of a medical treatment, the volume may be a group of cells or an area of tissue. If employed outside the medical field, the volume may be any area or region for which benefit may be achieved through an application of radiation.

In accordance with the present disclosure, a gantry may be provided. A gantry may refer to any apparatus configured to assist in directing radiation toward a target. The target to be irradiated may be, for example, a treatment volume such as a tumor within a patient's body. Because a system for treating a treatment volume with protons consistent with the present disclosure is just one application of the disclosed systems for generating a proton beam, it should be understood that this is merely an example. A gantry may also be used to direct a proton beam or other radiation beam toward any target to be irradiated.

In accordance with the present disclosure, a patient support platform may be provided. A patient support platform may refer to any surface, foundation, or other structure configured to support a patient during irradiation therapy. A patient support platform may be fixed, or it may be adjustable in any dimension.

Any of the systems in accordance with the present disclosure may comprise at least one processor configured to monitor, control, and/or facilitate the use of any component included in the system. Consistent with the disclosed embodiments, a processor may refer to any one or more processing devices, including, for example, an application specific integrated circuit (ASIC), a digital signal processor (DSP), a programmable logic device (PLD), a field programmable gate array (FPGA), a controller, a microprocessor, or other similar electronic devices and/or combinations thereof. A processor may comprise one or more modules of a control system.

In some embodiments consistent with the present disclosure, at least one processor may be configured to cause an electromagnetic radiation beam to strike individual patterned features that make up a plurality of patterned features an ion-generating target, and to thereby generate a resultant proton beam. In some embodiments consistent with the present disclosure, at least one processor may be configured to cause an electromagnetic radiation beam to strike one or more knife edges of an ion-generating target, and to thereby generate a resultant proton beam.

In some embodiments, at least one processor may control at least one of an electromagnetic radiation source and/or optics components. For example, a processor or group of processors may control at least one of the energy of an electromagnetic radiation beam, the flux of an electromagnetic radiation beam, the polarization of an electromagnetic radiation beam, the spatial profile of an electromagnetic energy beam, the temporal profile of an electromagnetic radiation beam, or other aspects of an electromagnetic radiation beam. More specifically, at least one processor may generate instructions to cause an electromagnetic radiation source to alter a spatial profile of an electromagnetic radiation beam by altering a spot size of the electromagnetic radiation beam. As another example, at least one processor may alter a temporal profile of an electromagnetic radiation beam by altering a chirp of the electromagnetic radiation beam. As a further example, at least one processor may alter a temporal profile of an electromagnetic radiation beam by altering a timing of one or more laser pump sources.

In embodiments consistent with the present disclosure, at least one processor may be configured to cause an adaptive mirror to direct an electromagnetic radiation beam at predetermined locations on a surface of an ion-generating target. For example, a processor or processors may be configured to cause an electromagnetic radiation beam to raster an ion-generating target. Such rastering may include sequential scanning of the electromagnetic radiation beam over contiguous patterned features making up a plurality of patterned features. Striking the individual patterned features may include, for example, continuously or discontinuously scanning a surface of an ion-generating target. In some embodiments, a processor may be configured to cause an adaptive mirror to adjust an electromagnetic radiation beam so as to strike patterned features individually, or it may be configured to strike individual patterned features simultaneously.

In accordance with the present disclosure, at least one processor may be configured to control multiple aspects of a system independently or simultaneously. For example at least one processor may be configured to adjust a flux of a proton beam while holding an energy of the proton beam substantially constant, or may be configured to adjust an energy of a proton beam while holding a flux of the proton beam substantially constant. Alternatively, at least one processor may be configured to adjust a flux of a proton beam and an energy of a proton beam simultaneously.

Figure 3:
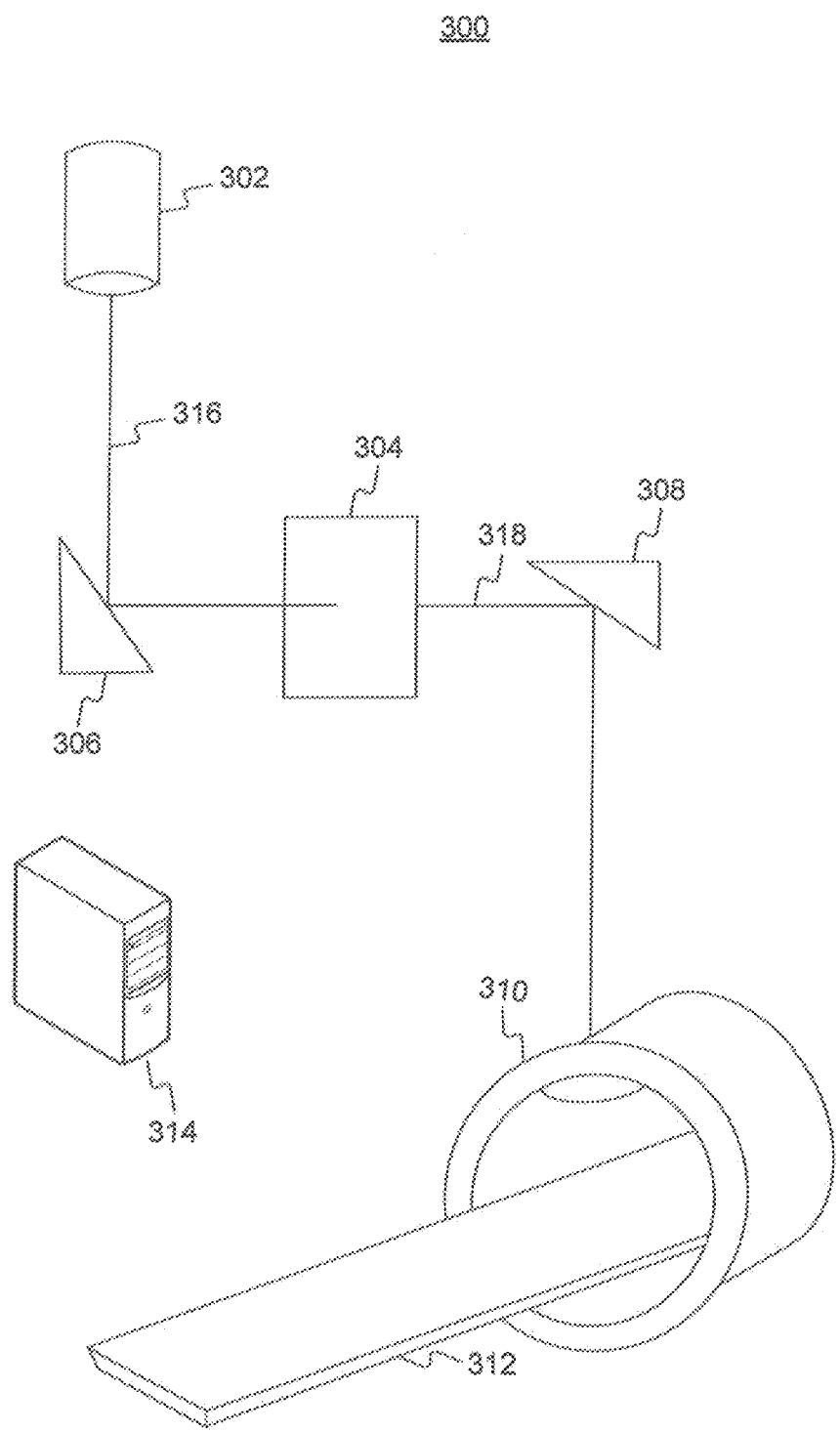
FIG. 3 is a diagram of an example of interconnected components of a system for providing proton therapy, consistent with disclosed embodiments.

FIG. 3 depicts an exemplary system 300 for providing proton therapy that includes an illustrative system for generating a proton beam. System 300 is also one example of a system for treating a treatment volume with protons. In accordance with disclosed embodiments, system 300 may include one or more of an electromagnetic radiation source 302, an ion-generating target 304, optics component(s) 306, proton beam adjustment component(s) 308, a gantry 310, a patient support platform 312, and a control system 314 configured to communicate with any one or more of the above.

A patient may be positioned on patient support platform 312. Patient support platform 312 may be any shape or form suitable for use with the other components of system 300 and conducive to supporting a patient during treatment. Patient support platform 312 may be fixed in place relative to gantry 310, or patient support platform 312 may be configured for translation and/or rotation prior to or during treatment. In some embodiments patient support platform 312 may be adjusted to accommodate patients of different sizes or to position a treatment volume in a path of a proton beam. Further, in some embodiments patient support platform 312 may be adjusted during treatment to reposition the treatment volume relative to the proton beam.

Gantry 310 may be configured to direct the proton beam toward a treatment volume, such as a tumor, within the patient's body. Gantry 310 may be configured to be manipulated in one or more ways to influence the proton beam's path, and may be composed of a number of materials and incorporate numerous components. Examples of gantry 310 consistent with embodiments of the disclosure are discussed in further detail below, which are not intended to be limiting.

Electromagnetic radiation source 302 may emit an electromagnetic radiation beam 316, for example, a laser beam, directed toward ion-generating target 304. In some embodiments, electromagnetic radiation source 302 may comprise one or more gas lasers (e.g., CO2 lasers), diode pumped solid state (DPSS) lasers (e.g., ytterbium lasers, neodymium-doped yttrium aluminium garnet lasers (Nd:YAG), or titanium-sapphire lasers (Ti:Sapphire)), and/or flash lamp pumped solid state lasers (e.g., Nd:YAG or neodymium glass). In a broader sense, any radiation source capable of causing a release of ions from a target may be employed.

An electromagnetic radiation source 302 may be selected based on its intensity, i.e. the energy divided by the temporal duration of the pulse and the spot size of the laser on the ion-generating target 304. A variety of combinations of spatial profile (e.g., spot size), wavelength, temporal duration, and energy may be used while still providing the same intensity. For example, in some embodiments, electromagnetic radiation beam 316 may be within an energy range of 1 J to 25,000 J, and a wavelength range of 400 nm to 10,000 nm. Electromagnetic radiation beam 316 may be pulsed, for example with a pulse width range of 10 fs to 100 ns. Electromagnetic radiation beam 316 may have various spot sizes. In some embodiments, a spot size between 1 $\mu m^2$ and 1 $cm^2$ may be used. Although spatial profiles of electromagnetic radiation beam 316 may have any beam profile, in some embodiments the spatial profile may include a Gaussian, super-Gaussian, Top Hat, Bessel, or annular beam profile.

In some embodiments, electromagnetic radiation source 302 may be configured to generate a main pulse after one or more pre-pulses. Contrast ratio (i.e., the ratio between the main pulse and the pre-pulses, also called a "pedestal" arriving before the main pulse) may influence proton generation. Contrast ratio may be more specifically defined the higher the intensity of the laser. As an example, on a timescale shorter than 100 ps, contrast ratio may range from $10^{-8}$ to $10^{-12}$.

As a more specific example, electromagnetic radiation source 302 may be a Ti:Sapphire laser. In the example of the Ti:sapphire laser, electromagnetic radiation beam 316 may be within an energy range of about 1 J to 25 J, and have a wavelength of about 800 nm. In this example, electromagnetic radiation beam 316 may have a pulse width range of about 10 fs to 400 fs, a spot size between about 2 $\mu m^2$ and 1 $mm^2$, and a Gaussian or Top Hat spatial profile. These properties are merely exemplary, and other configurations may be employed.

Electromagnetic radiation beam 316 may be directed to ion-generating target 304 by one or more optics component(s) 306 disposed, for example, along a trajectory between electromagnetic radiation source 302 and ion-generating target 304. Optics component(s) 306 may include one or more optical and/or mechanical components configured to alter properties of electromagnetic radiation beam 316, including spectral properties, spatial properties, temporal properties, energy, polarization, contrast ratio, or other properties. Optics component(s) 306 may be involved, for example, in generating, optimizing, steering, aligning, modifying, and or measuring electromagnetic radiation beam 316, or in other aspects of system 300. Optics component(s) 306 may include a wide variety of optical elements, such as lenses, mirrors, laser crystals and other lasing materials, piezo activated mirrors, plates, prisms, beam splitters, filters, light pipes, windows, blanks, optical fibers, frequency shifters, optical amplifiers, gratings, pulse shapers, XPW, Mazzler (or Dazzler) filters, polarizers, Pockels cells, optical modulators, apertures, saturable absorbers, and other optical elements.

Optics component(s) 306 may be fixed or adaptive. For example, optics component(s) 306 may include one or more active, adaptive, or reconfigurable components, such as deformable mirrors, plasma mirrors, Pockels cells, phase shifters, optical modulators, irises, shutters (manually and computer controlled), and other similar components. Adaptive properties may manipulate optic components themselves, as in the case of a deformable mirror or plasma mirror. The orientation of optics component(s) 306 may also be adjustable, such as by translating optics component(s) 306 or rotating optics component(s) 306 about a rotational axis. Adjustments may be manual or automated. As one example, control system 314 may receive a feedback signal and, in response, provide a control signal to a motor connected to optics component(s) 306 located between electromagnetic radiation beam 316 and the ion-generating target 304. Movement of the motor, in turn, may adjust optics component(s) 306 to alter the relative orientation between electromagnetic radiation beam 316 and the ion-generating target 304 (e.g., by repositioning the location of the laser-target interaction).

Examples of deformable mirrors that may be employed in optics component(s) 306 include, for example, segmented mirrors, continuous faceplate mirrors, magnetic mirrors, MEMS mirrors, membrane mirrors, bimorph mirrors, and/or ferrofluidic mirrors. Any number of other mirror technologies capable of altering the wave front of an electromagnetic radiation beam may also be used.

Examples of plasma mirrors that may be employed in optics component(s) 306 include a laser pulse focused onto an anti-reflective coated substrate, which ionizes so as to reflect and separate a high intensity peak from a lower intensity background of the pulse. As an example, a plasma mirror may be established by directing the laser pulse towards a parabolic mirror located in front of the anti-reflective coated substrate. Other ways of implementing a plasma mirror are also known to those of ordinary skill in the art, and are suitable for use with embodiments of the systems and methods described herein.

Optics component(s) 306 may be tailored to parameters related to an intended beam. For example, optics components 306 may be tailored in terms of wavelength, intensity, temporal pulse shape (e.g., pulse width), spatial size and energy distribution, polarization, and other properties of the intended beam. Such beam parameters may relate to an optics substrate material, size (e.g., lateral size or thickness), coating material (if any), shape (e.g., planar, spherical or other), orientation relative to a beam, or other specifications.

Optics component(s) 306 may include one or more corresponding holders configured to hold the element in place while allowing positioning of the element to an appropriate degree of accuracy, for example translation and rotation, as well as other degrees of freedom. In an embodiment, such holders may include opto-mechanical mounts held in place by an optical table or any other mechanical holder. Such degrees of freedom may be manipulated manually or via any appropriate automatic means, such as electric motors.

Optics component(s) 306 may be disposed in specific environmental conditions, such as a vacuum and/or an environment purged by one or more gasses. Furthermore, optics components 306 may be disposed in various places along the path of electromagnetic radiation source 302 between electromagnetic radiation source 302 and ion-generating target 304, or in any other system of system 300 where optical components are desired. Optics component(s) 306 may be configured for various uses, such as laser beam steering, laser beam diagnostics, laser-target interaction diagnostics, and/or ion-generating target viewing and positioning.

In some embodiments, the lifespan of optics component(s) 306 may vary. Some optics component(s) 306 may be long-term equipment, reused numerous times. Alternatively or additionally, some optics component(s) 306 may be consumable, used fewer times and replaced. Such classification may be based on a number of factors such as laser intensity and presence of debris/contamination. In some embodiments debris shielding may be installed proximate expensive or delicate optics to reduce a need for frequent replacements. Periodic examination may be performed for optics suspected to be damaged. Specialized optical systems may be installed to examine optics at risk.

Optics component(s) 306 may be manipulated manually, automatically, or by any combination thereof. Input types for manipulating optics components 306 may include high voltage signals, triggering signals, optical pumping, or any other form of input. Further, optics components 306 may be monitored by one or more cameras, such as CCD cameras. Automatic manipulation of adaptive mirror(s) may occur, for example, in response to one or more signals provided by the control system 314. The control system 314 may, for example, control one or more motor(s), piezoelectric element(s), microelectromechanical (MEMS) element(s), and/or the like associated with a deformable mirror. Alternatively or additionally, the control system 314 may, for example, control one or more laser pulse(s), anti-reflective coated substrate(s), and/or the like associated with a plasma mirror.

In some embodiments, optics component(s) 306 may include an adaptive deformable mirror, such as a deformable mirror having a plurality of facets, each of the plurality of facets being independently controllable. The facets may be controlled by digital control logic circuitry, such as digital control logic circuitry contained in control system 314. As another example, an adaptive mirror may be a plasma mirror that uses a focused laser pulse to ionize an anti-reflective coated substrate, thereby reflecting and separating a high intensity peak from a lower intensity background of the laser pulse. The laser pulse and/or anti-reflective coated substrate may be controlled by digital control logic circuitry, such as digital control logic circuitry contained in control system 314.

An adaptive mirror may be configured to direct the electromagnetic radiation beam 316 by one or more of adjusting a focus of the electromagnetic radiation beam, diverting the electromagnetic radiation beam, and scanning the electromagnetic radiation beam. The adaptive mirror may be configured to adjust focus of electromagnetic radiation beam in any way apparent to those of skill in the art. For example, electromagnetic radiation beam 316 may strike a plurality of facets of a deformable mirror, or electromagnetic radiation beam 316 may strike a plasma mirror. In some configurations, it may be desirable to adjust where electromagnetic radiation beam 316 is directed or to adjust a property of the electromagnetic radiation beam 316. A plurality of facets of a deformable mirror may be controlled to reflect electromagnetic radiation beam 316 such that its spot size at a desired location is smaller, larger, or differently shaped than its spot size just before striking the deformable mirror. Likewise, a plasma mirror may be controlled to reflect electromagnetic radiation beam 316 such that its spot size at a desired location is smaller, larger, or differently shaped than its spot size just before striking the plasma mirror.

The adaptive mirror may also be configured to divert electromagnetic radiation beam 316. For example, system 300 may be configured such that electromagnetic radiation beam 316 will sequentially or simultaneously strike a plurality of locations on ion-generating target 304 or a plurality of ion-generating targets 304 disposed in different locations within system 300. In such configurations, an adaptive mirror or other optics component(s) 306 may alter the path of electromagnetic radiation beam 316 to direct the beam onto the multiple locations and/or plurality of ion-generating targets. For example, an adaptive mirror or other optics component(s) 306 may sequentially divert (e.g., scan) electromagnetic radiation beam 316 from one location to an adjacent location in a pattern continuously or discontinuously, such as in a stepwise manner. In an automated process, control system 314 may be configured to cause the adaptive mirror to direct electromagnetic radiation beam 316 at predetermined locations on the surface of ion-generating target 304. For example, it may be advantageous to scan electromagnetic radiation beam 316 over a patterned array of ion-generating features provided at a surface of ion-generating target 304. It may also be advantageous to scan electromagnetic radiation beam 316 over an ion-generating target 304 that includes a plurality of ion-generating structures substantially oriented along a common axis, such as protrusions substantially extending away from a surface of the ion-generating target 304. It may also be advantageous to scan electromagnetic radiation beam 316 over an ion-generating target 304 patterned with one or more knife edges, such as an ion-generating target that includes one or more features having a narrow edge similar to an arête or the edge of a blade. The adaptive mirror is described as an example. Those of skill in the art will recognize that other optics component(s) 306 may perform the same or similar functions as those described above in reference to the adaptive mirror.

In accordance with the present disclosure, an ion-generating target may be configured to facilitate ion generation. For example, an ion-generating target may include a surface having one or more ion-generating structures or features. Such structures or features may be composed of one or more suitable materials, including ice (also referred to as snow), plastic, silicon, stainless steel or any of a variety of metals, carbon and/or any other material from which an ion beam may be generated. Such structures may be randomly arranged, arranged as defined by a growth or deposition process, and/or arranged in a patterned array. Such structures may alternatively or additionally include one or more narrow edges, similar to an arête or the edge of a blade. The structures may be configured based on one or more attributes of an electromagnetic radiation beam. For example, such structures may have a dimension smaller than a wavelength of an electromagnetic radiation beam, such as a laser.

Ion-generating target 304, when struck by electromagnetic radiation beam 316, may emit a variety of particles, including electrons, protons, x-rays, and other particles. Ion-generating target 304 may be composed of a variety of materials. Ion-generating target 304 may be configured such that it includes one or more individual features configured to interact with electromagnetic radiation beam 316. Alternatively or additionally, ion-generating target 304 may include a continuous surface or texture formed from a material favorable for interaction with electromagnetic radiation beam 316. Those of skill in the art will understand that there are numerous configurations that may be employed to emit particles upon interaction with an electromagnetic radiation beam, and that the disclosed embodiments are merely exemplary.

In some embodiments, ion-generating target 304 may be prefabricated. In other embodiments, ion-generating target 304 may be produced in situ within system 300 or an attached sample preparation system. For example, ion-generating target 304 may disposed within an interaction chamber, such as interaction chamber 1000, described below. This may involve forming an ion-generating target from a suitable material, including forming such material on a substrate. Such materials may include any gas, solid, or liquid chemical sources of the types commonly known in techniques such as evaporation, physical vapor deposition, chemical vapor deposition, molecular beam epitaxy, atomic layer deposition, and the like. For example, in embodiments in which ion-generating target 304 includes ice, materials used to form ion-generating targets may include water vapor ($H_2O$), hydrogen gas ($H_2$), and/or oxygen gas ($O_2$). Further, in embodiments in which ion-generating target 304 includes silicon, materials used to form ion-generating target 304 may include, for example, silane ($SiH_4$), disilane ($Si_2H_6$), trichlorosilane ($SiHCl_3$), or any other silicon source. Further still, in embodiments in which ion-generating target 304 includes plastic, sources may include, for example, polytetrafluoroethylene (PTFE) polymer source materials or any other PTFE source. As a person of ordinary skill in the art would recognize, these are just a few illustrative examples among many available target materials and target source materials. In addition, the interaction chamber may vary in structure to suit the form of the target employed. For example, when the target is ice, the interaction chamber may be specifically configured to maintain an appropriate temperature to support the ice. Each target material may have differing sustaining requirements, and therefore the structure of the interaction chamber may vary to suit the target.

FIG. 4. depicts illustrative ion-generating targets that may be employed as ion-generating target 304. For example, FIG. 4A shows an ion-generating target 402 including a cap structure 404 located over a hollow, hourglass-shaped cone 406. In one embodiment, a distance between at least two opposing points of the cone may be less than about 15 μm. In particular examples, the distance may be less than about 1 μm. In some embodiments, the features of ion-generating target 402 may be free standing. Such features may include, for example, any number of shapes, including cones, pyramids, hemispheres, and capped structures. The structures of illustrative ion-generating target 402 shown in FIG. 4 (as well as other embodiments of ion-generating target 304) may be formed using lithographic techniques, such as photolithographic techniques. In particular examples, an ion-generating target cone 406 may be fabricated on a silicon wafer 408, then coated with one or more metals 410. In some embodiments, protons may be ejected from a back-side opening 412. FIG. 4B depicts another illustrative ion-generating target suitable as ion-generating target 304 for use with the present invention. FIG. 4B depicts a portion of an ion-generating target having one or more micro-cone targets 420 on its surface. Each micro-cone target 420 may be suitable for producing a high energy, low divergence particle beam. In one embodiment, the micro-cone target 420 may include a substantially cone-shaped body 422 having an outer surface 424, an inner surface 426, a generally flat and round, open-ended base 428, and a tip 430 defining an apex. The cone-shaped body 422 may taper along its length from the generally flat and round, open-ended base 428 to tip 430, which defines the apex. Outer surface 424 and inner surface 426 may connect base 428 to tip 430.

FIGS. 4C, 4D, and 4E depict other illustrative ion-generating targets 304 suitable for use with embodiments of the present invention. Specifically, FIGS. 4C, 4D, and 4E depict surfaces of snow targets, which may be formed from crystals of ice. Ice may be advantageous for use as an ion-generating target because water is rich in hydrogen. Further, as shown in FIG. 4C, structures on the ion-generating target may exhibit a needle-like shape. Such a shape may enhance an electrical field generated by interaction of electromagnetic radiation beam 316 and ion-generating target 304. Individual needle-like structures on ion-generating target 304 may be approximately the same as a wavelength of electromagnetic radiation beam 316. As an example, structures may be approximately 1 μm to 10 μm.

Individual patterned features on the surface of ion-generating target 304 may be physically arranged on ion-generating target 304 such that they may be sequentially scanned. For example, such structures may be arranged in an array on a generally planar surface. Individual structures may be distributed evenly forming a pattern across an entire surface, as shown in FIG. 4C. Alternatively, structures may be arranged in a repeating pattern with space between the structures, as shown in FIGS. 4D and 4E.

Referring back to FIG. 3, proton beam adjustment component(s) 308 may include one or more components configured to form a proton beam 318 from protons generated by ion-generating target 304 and to direct the proton beam to gantry 310 and the treatment volume in the patient. Proton beam adjustment components 308 may include any equipment capable of manipulating charged particles, such as protons. For example, proton beam adjustment component(s) 308 may include electromagnetic components. More specifically, proton beam adjustment component(s) 308 may include one or more electromagnetic constituents, such as a quadrupole lens, cylindrical mirror lens/analyzer ("CMA"), spherical mirror lens/analyzer ("SMA"), collimator, energy degrader, time-of flight control unit, magnetic dipole, or any other component suitable for manipulating charged ions. Proton beam adjustment component(s) 308 may also adjust one or more properties of the proton beam 318. For example, beam adjustment components 308 may manipulate properties such as flux or spot size. Proton beam adjustment component(s) 308 may also filter particles having particular energies or reduce the energy of various particles.

Proton beam adjustment component(s) 308 may be disposed in various locations within system 300, including inside an interaction chamber, along a proton beam line, within gantry 310, or any combination thereof. For example, proton beam adjustment components may be disposed along a beam line extending between ion-generating target 304 and gantry 310. The beamline may be configured to maintain various conditions such as temperature, pressure (e.g., vacuum), or other condition(s) conducive to propagating and/or manipulating proton beam 318. The beam line may further include other components for housing charged particle beams, including, but not limited to, elements such as beam dumps, beam attenuators, and protective shielding.

Control system 314 may monitor and/or control various aspects of system 300. For example, control system 314 may monitor various detectors associated with electromagnetic radiation source 302, optics component(s) 306, ion-generating target 304, proton beam adjustment component(s) 308, gantry 310, and/or patient support platform 312. Control system 314 may also accept input from a user of system 300, such as a technician or other operator. Control system 314 may also accept, store, and execute operations pertaining to system 300, including, for example, initiating and maintaining any functionalities of system 300. Control system 314 may also be configured to implement feedback between one or more detectors and one or more of the various components of system 300. For example, such feedback may improve precision, efficiency, speed, and/or other aspects of system 300 or its operation. Examples of such feedback are described in greater detail below.

Figure 5:
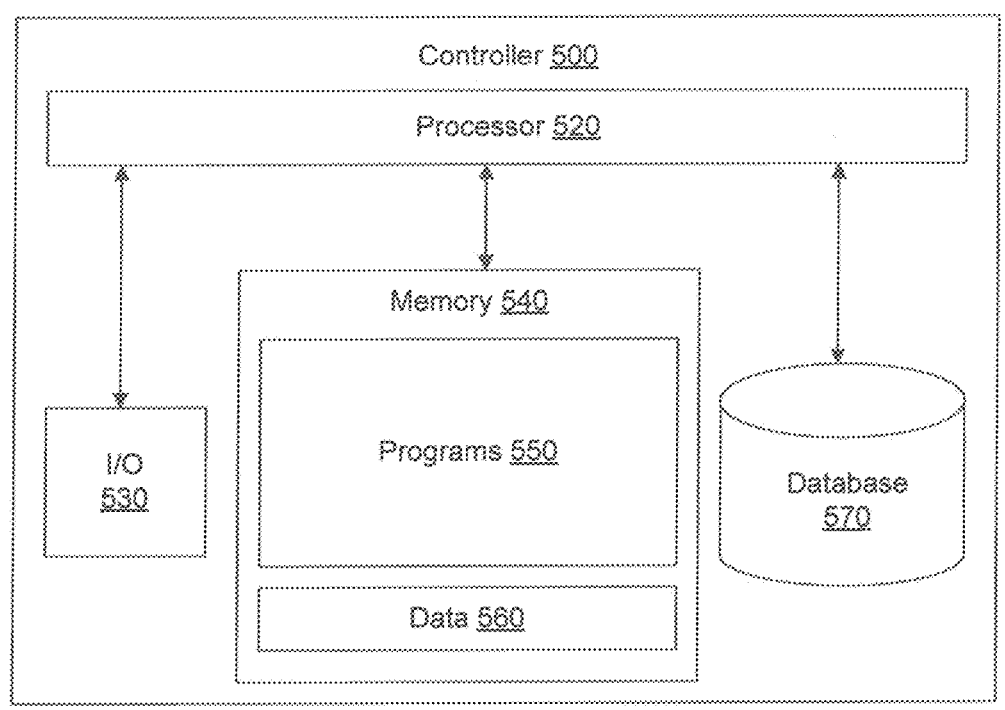
FIG. 5 is a schematic diagram of an example of a controller for controlling a proton therapy system, consistent with disclosed embodiments.

FIG. 5 is a diagram of an exemplary computing system 500, illustrating a configuration that may be associated with control system 314 and consistent with disclosed embodiments. As a person of ordinary skill will understand, some or all of the functions associated with control system 314 may be executed or facilitated by software, hardware, or any combination thereof, associated with computing system 500. In one embodiment, computing system 500 may have one or more processors 520, one or more memories 540, and one or more input/output (I/O) devices 530. In some embodiments, computing system 500 may take the form of a server, general purpose computer, customized dedicated computer, mainframe computer, laptop, mobile device, or any combination of these components. In certain embodiments, computing system 500 (or a system including computing system 500) may be configured as a particular apparatus, system, or the like based on the storage, execution, and/or implementation of software instructions that may perform one or more operations consistent with the disclosed embodiments. Computing system 500 may be standalone, or it may be part of a subsystem, which may be part of a larger system.

Processor 520 may include one or more known processing devices, such as an application specific integrated circuit (ASIC), a digital signal processor (DSP), a programmable logic device (PLD), a field programmable gate array (FPGA), a processor, a controller, a microprocessor, other electronic units and combination thereof. For example processor 520 may include a processor from the Pentium™ or Xeon™ family manufactured by Intel™, the Turion™ family manufactured by AMD™, or any of various processors manufactured by Sun Microsystems. Processor 520 may constitute a single core or multiple core processor that executes parallel processes simultaneously. For example, processor 520 may be a single core processor configured with virtual processing technologies. In certain embodiments, processor 520 may use logical processors to simultaneously execute and control multiple processes. Processor 520 may implement virtual machine technologies, or other known technologies to provide the ability to execute, control, run, manipulate, store, etc. multiple software processes, applications, programs, etc. Processor 520 may include a multiple-core processor arrangement (e.g., dual, quad core, etc.) configured to provide parallel processing functionalities to allow computing system 500 to execute multiple processes simultaneously. One of ordinary skill in the art would understand that other types of processor arrangements could be implemented that provide for the capabilities disclosed herein. The disclosed embodiments are not limited to any type of processor(s).

Memory 540 may include one or more storage devices configured to store instructions used by processor 520 to perform functions related to the disclosed embodiments. For example, memory 540 may be configured with one or more software instructions, such as program(s) 550 that may perform one or more operations when executed by processor 520. The disclosed embodiments are not limited to separate programs or computers configured to perform dedicated tasks. For example, memory 540 may include a program 550 that performs the functions of computing system 500, or program 550 could comprise multiple programs. Additionally, processor 520 may execute one or more programs located remotely from computing system 500. For example, controller 314, may, via computing system 500 (or variants thereof), access one or more remote programs that, when executed, perform functions related to certain disclosed embodiments. Processor 520 may further execute one or more programs located in a database 570. In some embodiments, programs 550 may be stored in an external storage device, such as a server located outside of computing system 500, and processor 520 may execute programs 550 remotely.

Memory 540 may also store data that may reflect any type of information in any format that the system may use to perform operations consistent with the disclosed embodiments. Memory 540 may store instructions to enable processor 520 to execute one or more applications, such as server applications, network communication processes, and any other type of application or software. Alternatively, the instructions, application programs, etc., may be stored in an external storage (not shown) in communication with computing system 500 via a suitable network, including a local area network or the internet. Memory 540 may be a volatile or non-volatile, magnetic, semiconductor, tape, optical, removable, non-removable, or other type of storage device or tangible (i.e., non-transitory) computer-readable medium.

Memory 540 may include data 560. Data 560 may include any form of data used by controller 314 in controlling ion (e.g., proton) therapy treatment via system 300. For example, data 560 may include data related to operation of various components of system 300, feedback parameters associated with various components of operating system 300, data gathered from one or more detectors associated with system 300, treatment plans for particular patients or for particular diseases, calibration data for various components of system 300, etc.

I/O devices 530 may include one or more devices configured to allow data to be received and/or transmitted by computing system 500. I/O devices 530 may include one or more digital and/or analog communication devices that allow computing system 500 to communicate with other machines and devices, such as other components of system 300 shown in FIG. 3. For example, computing system 500 may include interface components, which may provide interfaces to one or more input devices, such as one or more keyboards, mouse devices, displays, touch sensors, card readers, biometric readers, cameras, scanners, microphones, wireless communications devices, and the like, which may enable computing system 500 to receive input from an operator of controller 314. Further, I/O devices may include one or more devices configured to allow control system 314 to communicate with one or more of the various devices of system 300, such as through wired or wireless communication channels.

Computing system 500 may also contain one or more database(s) 570. Alternatively, computing system 500 may be communicatively connected to one or more database(s) 570. Computing system 500 may be communicatively connected to database(s) 570 via a network such as a wired or wireless network. Database 570 may include one or more memory devices that store information and are accessed and/or managed through computing system 500.

Figure 6:
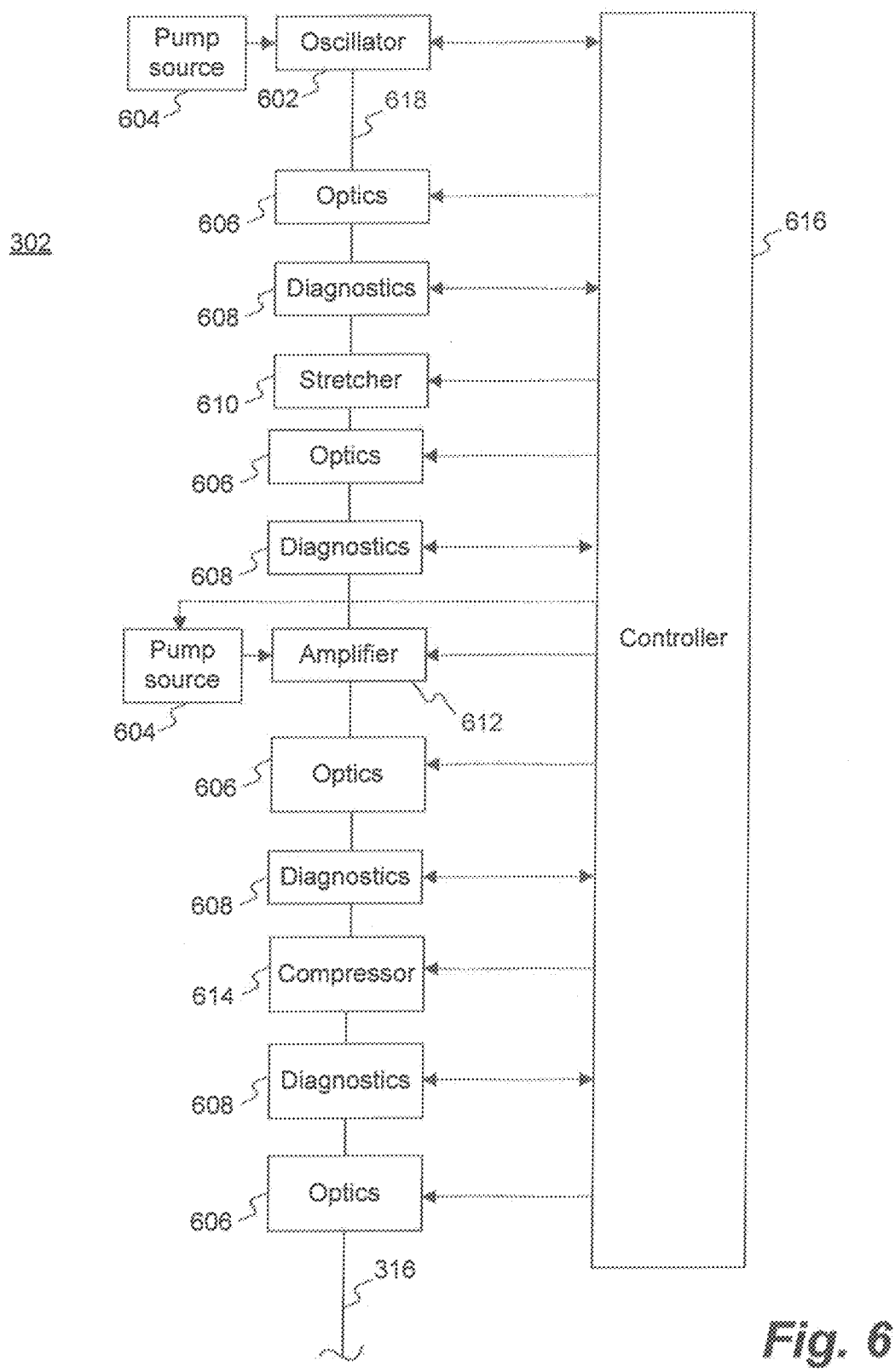
FIG. 6 is a schematic diagram of an example of an electromagnetic radiation source, consistent with disclosed embodiments.

FIG. 6 is a general schematic of an exemplary electromagnetic radiation source 302. As shown in FIG. 6, electromagnetic radiation source 302 may include one or more oscillators 602, pump sources 604, optics components 606, diagnostics components 608, stretchers 610, amplifiers 612, compressors 614, and controllers 616. The configuration of FIG. 6 is merely an example, and numerous other configurations may be implemented consistent with the disclosed embodiments, incorporating one or more of the components of electromagnetic radiation source 302, system 300, or other components.

Oscillator 602 may include one or more lasers for generating an initial laser pulse 618 to be manipulated (e.g., shaped and/or amplified) to reach requirements for electromagnetic radiation beam 316. A wide variety of lasers or laser systems may be used as oscillator 602, including commercial available laser systems.

Pump source 604 may include independent lasers or laser system(s) configured to transfer energy into laser pulse 618. In some embodiments, pump source 604 may be connected to the output of oscillator 602 by an optical beamline incorporating one or more of optics component(s) 306. Additionally or alternatively, pump source 604 may include other pump mechanisms such as flash lamps, diode lasers, and diode-pumped solid-state (DPSS) lasers, or the like. In some embodiments, pump source 604 may be configured to alter a temporal profile of electromagnetic radiation beam 316. For example, control system 314 may be configured to control a timing of pump source 604, thereby controlling the timing of a pre-pulse and a pedestal of the electromagnetic radiation beam.

Optics components 606 may include any of the components discussed in relation to optics components 306, and may perform any of the roles and/or functions described in relation to optics components 306.

Diagnostics 608 may include optical, opto-mechanical, or electronic components designed to monitor laser pulse 618, such as, for example its temporal and spatial properties, spectral properties, timing, and/or other properties. More specifically, diagnostics 608 may include one or more photodiodes, oscilloscopes, cameras, spectrometers, phase sensors, auto-correlators, cross-correlators, power meters or energy meters, laser position and/or direction sensors (e.g., pointing sensors), dazzlers (or mazzlers), etc. Diagnostics 608 may also include or incorporate any of the components identified above with respect to optics components 606.

Stretcher 610 may be configured to chirp or stretch laser pulse 618. More specifically, stretcher 610 may include diffraction grating(s) or other dispersive components, such as prisms, chirped mirrors, and the like.

Amplifier 612 may comprise an amplification medium such as, for example, titanium sapphire crystal, $CO_2$ gas, or Nd:YAG crystal. Amplifier 612 may also include a holder for the amplification medium. The holder may be configured to be compatible with supporting environmental conditions such as positioning, temperature, and others. Amplifier 612 may be configured to receive energy from pump source 604 and transfer this energy to laser pulse 618.

Compressor 614 may include an optical component configured to compress laser pulse 618 temporally, for example to a final temporal duration. Compressor 614 may be constructed from diffraction gratings positioned on holders and positioned in a vacuum chamber. Alternatively, compressor 614 may, for example, be constructed of dispersion fibers or prisms. In addition, the compressor 614 may include mirrors or other optics components 306, as well as motors, and other electronically controlled opto-mechanics.

Controller 616 may include electronic system(s) that control and/or synchronize various components of electromagnetic radiation source 302. Controller 616 may include any combination of controllers, power supplies, computers, processors, pulse generators, high voltage power supplies, and other components. As an example, controller 616 may include one or more computing systems 500, which may be dedicated to electromagnetic radiation source 302 or shared with other components of system 300. In some embodiments, some or all of the functions of controller 616 may be performed by controller 314 of system 300.

Controller 616 may interface with various components of electromagnetic radiation source 302 and other components of system 300 via various communication channels. The communication channels may be configured to transmit electrical or other signals to control various optical and opto-mechanical components associated with radiation source 302 or system 300. The communication channels may include a conductor compatible with high voltage, electrical triggers, various wired or wireless communication protocols, optical communications, and other components. Controller 616 may receive input from optical and mechanical diagnostics along electromagnetic radiation source 302, and from diagnostics 608 along other parts of system 300. Further, controller 616 may receive signals from or based on input from a user, for example signals based on a patient treatment plan input by a user.

Figure 7:
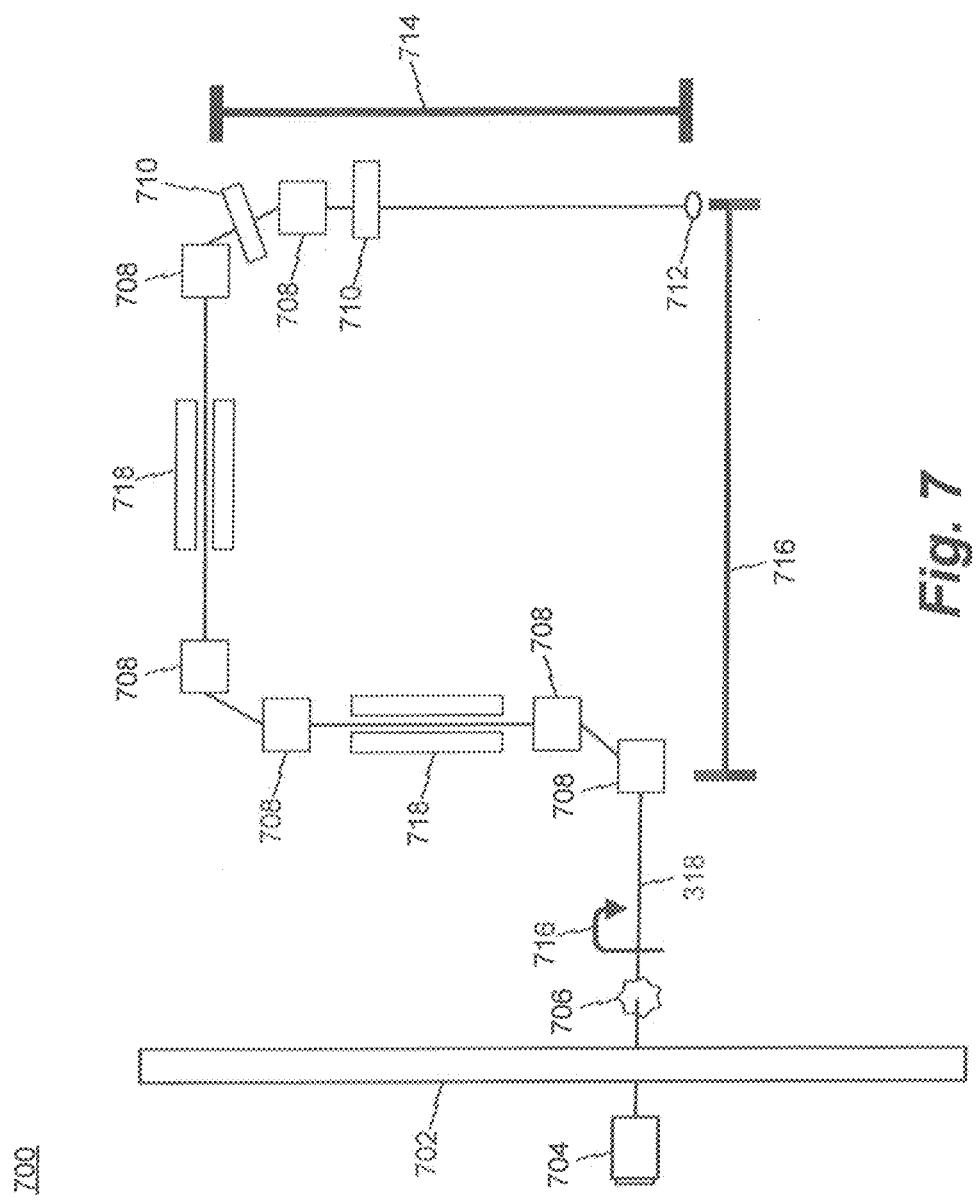
FIG. 7 is a schematic diagram of an example of a gantry, consistent with disclosed embodiments.

FIG. 7 depicts an example of a gantry 700, consistent with embodiments of the present disclosure. In some embodiments, gantry 310 (FIG. 3) may be arranged in the form of gantry 700, although this is not intended to be limiting, and other gantry designs may be employed. Gantry 700 may deliver proton beam 318 to an isocenter 712. In some embodiments, isocenter 712 may represent the location of a treatment volume or a location within a treatment volume. Gantry 700 may also be configured for beam adjustment and reconfiguration for appropriately directing proton beam 318 prior to and during a treatment. Gantry 700 may include a solenoid 704, a coupling 706, beam adjustment component(s) 708, collimator(s) 718, and scanning magnet(s) 710. Height 714 and width 716 may vary widely based on numerous possible configurations of gantry 700. In some embodiments either or both of height 714 and width 716 may be as little as 2.5 meters.

In some embodiments, gantry 700 may be separated from other components of system 300 by a wall 702, or other barrier. Wall 702 may include one or more openings (not shown in figures) to allow passage of proton beam 318 and any beam line or other equipment configured to deliver proton beam 318. Location of wall 702 may vary, depending on a number of factors and in some embodiments wall 702 may not be present.

Solenoid 704 may be configured to capture protons emitted by ion-generating target 304. In some embodiments, protons emitted by ion-generating target 304 may exhibit a large divergence. As an example, beam size of protons emitted from ion-generating target 304 may expand by a factor of 100 over a short distance, such as 1 cm. Solenoid 704 may be configured to reduce convergence of proton beam 318.

Solenoid 704 may include a high-field solenoid, such as, for example, a superconducting solenoid at 9 to 15 T. Field strength may be related to solenoid length and resulting beam size. Higher solenoid field strength may result in smaller beam size and aperture required in solenoid 704. Solenoid 704 may vary in length based on field strength and other factors. In some embodiments, solenoid 704 may be between 0.55 m and 0.85 m in length with an aperture between 4 cm and 20 cm. In some embodiments, solenoid 704 may be used in conjunction with one or more collimators. Further, in some embodiments, one or more quadrupoles may be employed in addition to or as an alternative to solenoid 704.

Coupling 706 may be any mechanical and or optical connection configured to facilitate physical movement of gantry 700, such as rotation about an axis of rotation, such as axis 716. Gantry may be configured to be physically moved by any appropriate arrangement of motors and/or actuators, which may be controlled by control system 314. Coupling 706 may include one or more bearings or bushings and may be connected to and/or integrated into a beam line carrying proton beam 318. Therefore, coupling 706 may be configured to maintain a seal or other barrier to prevent loss of a vacuum state or other environmental conditions within the beam line. Further, coupling 706 may include rotationally invariant optics, for example to reduce tune dependence as a function of gantry position.

Gantry 700 may further include beam adjustment component(s) 708. Beam adjustment components 708 may include any of beam adjustment components 308 discussed above, configured to guide proton beam 318 through the gantry. In some embodiments, beam adjustment components 708 may include electromagnets, such as dipoles and/or quadrupoles, configured to divert proton beam 318 through gantry 700. Beam adjustment components 708 may include normal conducting dipoles, superferric superconducting dipoles, stripline dipoles, etc.

In some embodiments, beam adjustment components 708 may include dipole pairs (e.g., each bending proton beam 318 by approximately 45°) to form a rectangle (or any other combinations of angles to form a rectangle or another desired shape). The dipole pairs may operate at about 4.8 T and be about 0.6 m long. Straight sections between dipole pairs may be adjusted independently, providing tuning range, flexibility and therefore customization in the electromagnetic optics. Splitting 90° bends into two may improve reference trajectory control, as each dipole may be adjusted independently, for example via shunts on a single power supply, providing at least 10% variation (20% total relative change considering two). Thus, dipole pairs may facilitate independent trajectory correction on each arm of gantry 700, decreasing tolerances and cost.

Gantry 700 may also include one or more collimators 718. Collimators 718 may be configured to filter proton beam 318 such that only protons traveling in a desired direction and/or having a desired momentum are allowed to pass. Collimators 718 may be disposed in a variety of locations within gantry 700. For example, if beam adjustment components 708 have achromatic properties producing undesired effects on the beam downstream, collimators 718 may be configured to counteract such effects.

Gantry 700 may further include scanning magnet(s) 710. Scanning magnets 710 may include beam adjustment components, such as beam adjustment components 308 or 708, configured to adjust isocenter 712's location in space. Scanning magnets 710 may be controlled by control system 314, for example to adjust location of treatment being provided to a treatment volume. Scanning magnets 710 may be disposed in any of a number of locations within gantry 700. For example, scanning magnets 710 may be upstream from one or more of beam adjustment components 708, downstream of all of beam adjustment components, or a combination of such upstream and downstream locations, as shown in FIG. 7.

System 300 may be configured such that scanning magnets are operated in cooperation with other components in order to control the location of treatment within a patient. For example, control system 314 may control any combination of scanning magnets 710, movement of gantry 700, and movement of patient support platform 312. One or more components may be configured for control of particular dimensions and/or degrees of freedom. For example, patient support platform may be configured to adjust patient position in one dimension, while scanning magnets 710 adjust in another dimension, orthogonal to the first.

Alternatively or additionally, system 300 may be configured such that a coarse adjustment in a given dimension may be performed by a different component than a fine adjustment. For example, a coarse adjustment in a particular dimension may be performed by a motor configured to manipulate patient support platform 312, while fine adjustment may be performed by a scanning magnet 710. Numerous combinations of such adjustments will be apparent to those of skill in the art.

Figure 8:
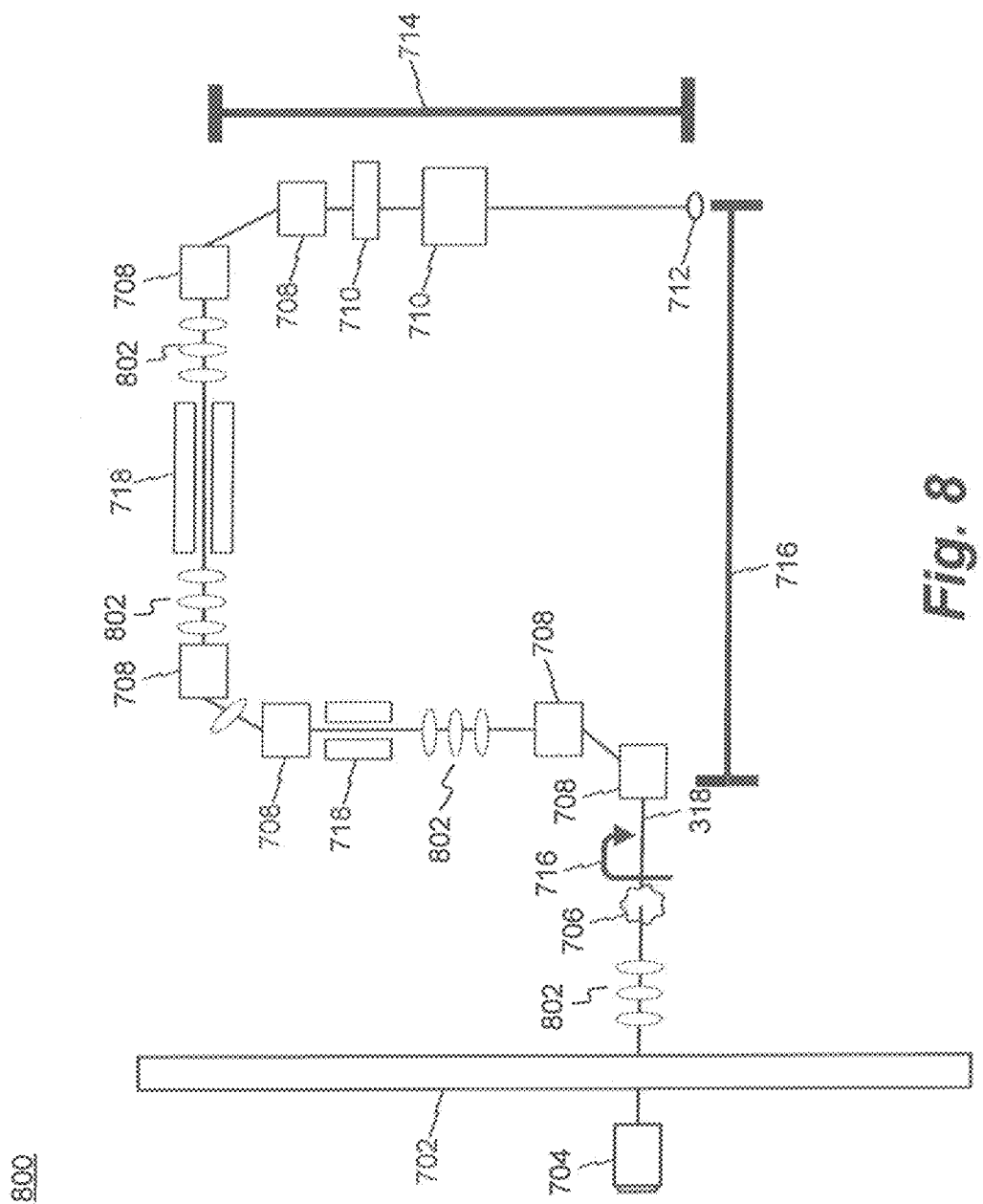
FIG. 8 is a schematic diagram of another example of a gantry, consistent with disclosed embodiments.

FIG. 8 depicts a further example of a gantry 800. Gantry 800 may include some or all of the same components as gantry 700, such as solenoid 704, coupling 706, beam adjustment component(s) 708, collimator(s) 718, and scanning magnet(s) 710, and may further include additional quadrupole elements 802. Quadrupole elements 802 are magnetic elements that are part of the magnetic beam line and help deliver the proton beam to the treatment volume. Quadrupole elements 802 are typically used to focus or de-focus a beam of charged particles, as opposed to some larger dipoles that may often be used as bending magnets to bend the proton beam. Quadrupole elements 802 may be permanent magnets (e.g., made of rear-earth elements and/or other magnetic materials), normal-conducting electromagnets, super-conducting electromagnets, pulsed magnets, or other devices capable of providing the appropriate fixed or tunable magnetic field.

Figure 9:
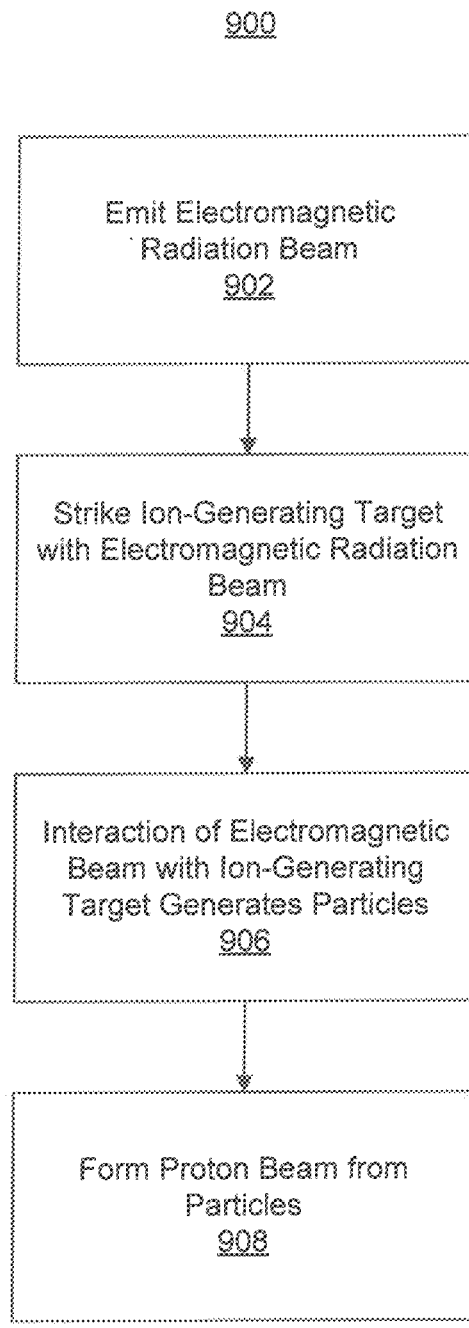
FIG. 9 is a flowchart of an example of a proton therapy process, consistent with disclosed embodiments.

FIG. 9 is an exemplary flow chart of a process 900 for proton beam formation. In step 902, an electromagnetic radiation source (e.g., source 302) may emit an electromagnetic radiation beam (e.g., beam 316). In step 904, the electromagnetic radiation beam may strike ion-generating target (e.g., target 304). In step 906, interaction of the electromagnetic radiation beam with the ion-generating target may generate particles, including protons. In step 908, proton beam adjustment component(s) (e.g., components 308) may form a proton beam (e.g., beam 318) from the particles and direct the proton beam to the treatment volume in the patient. The steps of process 900 may be carried out automatically, such as by control system 314. The steps of process 900 may also be carried out in response to user input, such as through control system 314 or carried out by a combination of automatic and manual operation of various components. In some embodiments, process 900 may be carried out based on specifications in a treatment plan, which may be customized to varying degrees based on a particular patient, treatment type, and/or treatment volume.

The electromagnetic radiation beam emitted in step 902 may be generated via any components capable of radiation beam generation, such as, for example, various combinations of the components described in relation to FIG. 6.

In step 904, the electromagnetic radiation beam may strike and ion-generating target. For example, ion-generating target 304 may be disposed within an interaction chamber, isolating the ion-generating target from the outside environment. Upon striking ion-generating target 304, an interaction of electromagnetic radiation beam 316 and ion-generating target 304 may generate various particles, including protons that may be used in proton beam 318. In some embodiments, protons may be emitted at a proton energy of about 250 MeV from a location on ion-generating target 304 struck by electromagnetic radiation beam 316 focused to a spot size of about 10 to 100 µm. The two-dimensional divergence angle of protons emitted from ion-generating target 304 may be about 0.2 radians (i.e., about 11 degrees). In addition, proton energy angular distribution $\partial\Omega/\partial E$ and proton number energy distribution $\partial N/\partial E$ may be very small so that the energy angular distribution and proton number energy distribution are reasonably constant. As an example, a pulse of electromagnetic radiation beam may result in the emission of $10^8$ protons, and pulses may be repeated at a rate of 10 to 1000 Hz. Accordingly, a pulsed electromagnetic radiation beam 316 may thereby produce a pulsed proton beam 318. A pulse of protons may also be referred to as a proton "bunch."

In accordance with the present disclosure, an ion-generating target may be supported by and/or housed within an interaction chamber. As used in the present disclosure, an interaction chamber may refer to any structure configured to isolate the target from ambient conditions and to provide an appropriate environment for ion generation.

In accordance with the present disclosure, the interaction chamber may, for example, comprise a target stage. As used in the present disclosure, a target stage may refer to any structure configured to support an ion-generating target. In some embodiments, a target stage may be controlled by a processor configured to cause relative movement between the target stage and an electromagnetic radiation beam.

In accordance with the present disclosure, the interaction chamber may comprise one or more detectors. As used herein, a detector may refer to a device that detects one or more properties of a sample chamber condition, an electromagnetic radiation source or beam, a proton beam, and/or a laser-target interaction. A detector may, for example, observe any condition within and/or proximate to the interaction chamber. In some embodiments, a system for generating a proton beam may include other detectors separate from an interaction chamber. As an example, a detector may be configured to measure at least one laser-target interaction property.

As used in the present disclosure, a laser-target interaction may refer to an observable property related to the interaction of an electromagnetic radiation beam with an ion-generating target. Laser-target interaction properties may include, for example, a proton beam property, a secondary electron emission property, an x-ray emission property, a proton beam energy, a proton beam flux, and/or other property indicative of the interaction between an electromagnetic radiation beam and an ion-generating target.

Figure 10:
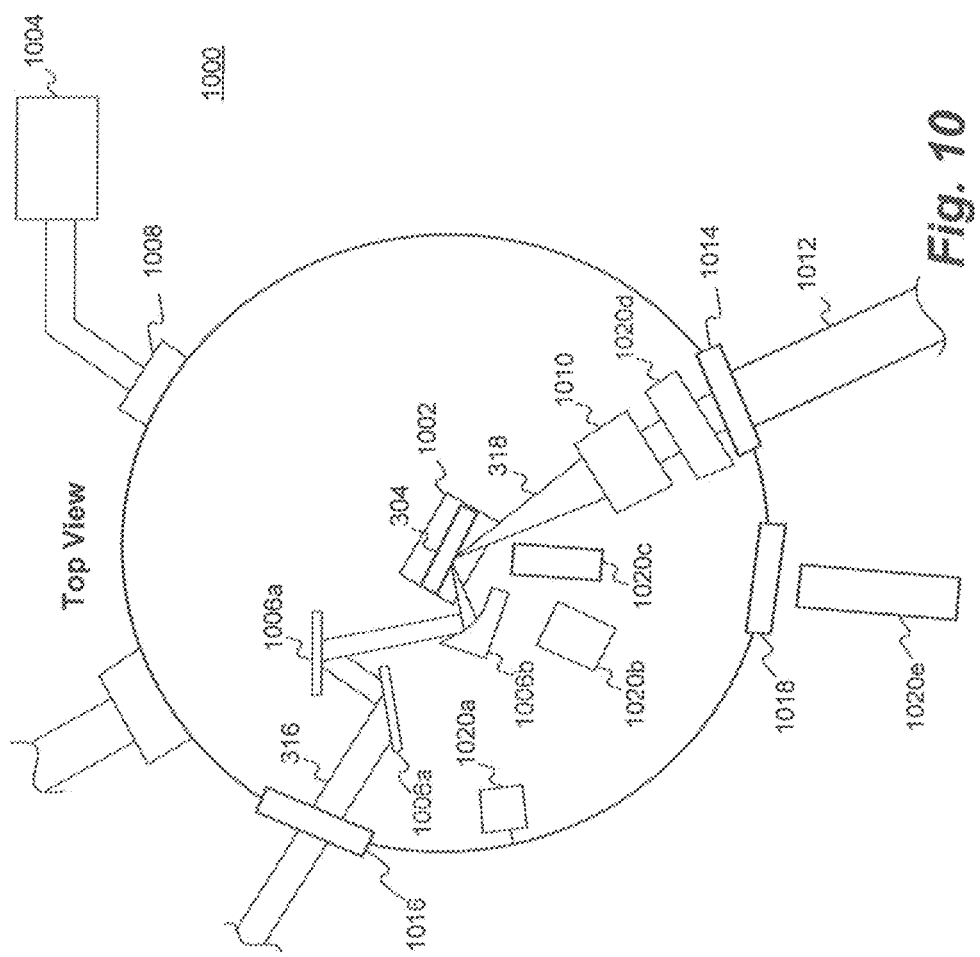
FIG. 10 illustrates aspects of an example of an interaction chamber, consistent with disclosed embodiments.

FIG. 10 depicts an example of an interaction chamber 1000. Interaction chamber 1000 may be any size and shape, and may be constructed of any appropriate material or materials capable of housing a target during laser-target interaction. Stainless steel is one example of a material that may be used to construct the interaction chamber 1000.

Interaction chamber 1000 may include one or more stages 1002 configured to support ion-generating target 304 and/or other equipment within interaction chamber 1000, such as optics component(s), beam adjustment component(s), detectors, or the like. Stage(s) 1002 may be fixed or adjustable. An adjustable stage may be configured for translation and/or rotation along one or more axes. Adjustment of stage(s) 1002 may be manual or automated. Automated adjustment may be performed, for example, in response to one or more signals provided by control system 314. Stage(s) 1002 may optionally be configured to heat, cool, or maintain the temperature of ion-generating target 304. Temperature control may be achieved, for example, by monitoring the temperature of ion-generating target 304 and raising, lowering, or maintaining the temperature of ion-generating target 304 in response to the measured temperature. Temperature monitoring can be achieved, for example, with one or more thermocouples, one or more infrared temperature sensors, and/or any other technique used to measure temperature. Temperature adjustment may be made, for example, by adjusting the amount of electric current flowing through a heating element. The heating element may be, for example, a refractory metal such as tungsten, rhenium, tantalum, molybdenum niobium, and/or alloys thereof. Temperature adjustment may also be made, for example, by flowing a coolant, such as water or a cryogenic fluid (e.g., liquid oxygen, liquid helium, liquid nitrogen, etc.) through a conduit directly or indirectly placed in thermal communication with ion-generating target 304. As a person of ordinary skill in the art would appreciate, these exemplary manners of adjusting temperature are compatible and may be combined. Of course, these temperature adjustment methods are not limiting, and any other known method for heating, cooling, and or maintaining the temperature of ion-generating target 304 may be used with the disclosures herein.

Interaction chamber 1000 may include one or more associated vacuum pump(s) 1004. For example, either or both of sample preparation and proton beam formation may have sub-atmospheric atmospheric pressure requirements or may achieve optimal performance within a particular range of sub-atmospheric pressures. Vacuum pump(s) 1004 may be used to influence pressure conditions within interaction chamber 1000 and/or components associated with interaction chamber 1000. For example, vacuum pump(s) 1004 may maintain a vacuum condition or near-vacuum condition in interaction chamber 1000. Examples of vacuum pump(s) 1004 may include one or more turbo-molecular pumps, cryogenic pumps, ion pumps, or mechanical pumps, such as diaphragm or roots pumps. Vacuum pump(s) 1004 may operate in conjunction with one or more pressure regulators (not shown in figures).

Interaction chamber 1000 may include optics components 1006. Any of the components noted above with respect to optics component(s) 306 may be used inside the interaction chamber to further direct electromagnetic radiation beam 316. For example, as shown in FIG. 10, interaction chamber may include mirrors 1006a configured to direct electromagnetic radiation beam 316 toward ion-generating target 304. In an embodiment, interaction chamber 1000 may include a parabolic mirror 1006b configured to focus electromagnetic radiation beam 316 onto ion-generating target 304.

Interaction chamber 800 may include any number of proton beam adjustment component(s) 308. For example, as shown in FIG. 8, interaction chamber 1000 may include a collimator 1010. Those of skill in the art will appreciate that alternatively or additionally, other proton beam adjustment component(s) 308 may be included in interaction chamber 800. In various embodiments, any of the beam adjustment component(s) 308 may be incorporated into interaction chamber 1000.

Interaction chamber 1000 may include or interface with a beam line 1012, as described above in association with proton beam adjustment component(s) 308. Beam line 1012 may include a conduit maintained at sub-atmospheric pressures to facilitate propagation of proton beam 318. Beam line 812 may include proton beam adjustment components, such as any of the elements referenced above with respect to proton beam adjustment component(s) 308. Beam line 812 may also include vacuum pumps, such as any of the pumps described in relation to vacuum pump(s) 1004, to achieve and/or maintain sub-atmospheric conditions.

Interaction chamber 1000 may include one or more valve(s) 1014. Any suitable valve(s) may be used, and may be located, for example, between various portions of interaction chamber 1000 or between interaction chamber 1000 and other components of system 300 or its ambient environment. Valve(s) 1014 may be configured, for example, to isolate vacuum pump(s) 1004 or beam line 1012. Valve(s) 1014 may be manual or automatic. Automatic valves may be, for example, pneumatic and/or electronic. Valve(s) 1014 may be simple open/close valves, such as a two-position gate valve, or valve(s) 1014 may be configured to be partially open. Valve(s) 1014 associated with vacuum pump(s) 1004 may, for example, include one or more butterfly valve(s) that can vary continuously between open and closed states. Valve(s) 1014 may be configured to maintain pressure, retain or release materials, and/or allow access to interaction chamber 800 for maintenance of parts or replacement of ion-generating targets.

Interaction chamber 1000 may include one or more shutter(s) 1016. Shutter(s) 1016 may be configured, for example, to block or allow electromagnetic radiation beam 1016 into chamber 1000. Shutter(s) 1016 may be, for example, a simple open/close shutter. Shutter(s) 1016 may also be configured to chop electromagnetic radiation beam 316 if desired. Operation of shutter(s) 1016 may be manual or automated. Automated operation may occur, for example, in response to one or more signals provided by control system 314.

Interaction chamber 1000 may include one or more windows 1018. Windows 1018 may be composed of any material suitable for the pressure, temperature, and other environmental factors associated with interaction chamber 1000.

As described above, interaction chamber 1000 may be configured for forming an ion-generating target in situ. System 300 may also include a separate or substantially separate preparation chamber (not shown in FIG. 6 or 10) connected to interaction chamber 1000 and configured for target preparation and/or conditioning. The preparation chamber may include various equipment and instrumentation for preparing ion-generating targets, such as equipment that may be found in systems for performing evaporation, physical vapor deposition, chemical vapor deposition, molecular beam epitaxy, atomic layer deposition, and the like. The preparation chamber may also include one or more stage(s) for holding ion-generating target 304 or a target substrate that will serve as a template to form ion-generating target 304. The preparation chamber may also include mechanisms for transferring the ion-generating target into place in the interaction chamber following preparation. Alternatively or in addition to using a separate or substantially separate preparation chamber, interaction chamber 1000 may be similarly equipped so that sample preparation or conditioning may take place within interaction chamber 1000 (not shown in FIG. 6 or 10).

The preparation chamber may also include temperature control elements (as described above with respect to stages 1002), one or more sample transfer mechanisms, such as a transfer arm or any other transfer device well known by those familiar with vacuum systems. System 300 may also include a load lock between sample preparation chamber and interaction chamber 1000.

Interaction chamber 1000 may further include heating and or cooling elements (not shown in FIG. 10). Either or both of sample preparation and particle beam formation may have temperature requirements or may achieve optimal performance within a particular range of temperatures. Interaction chamber may include heating elements and/or cooling elements configured to achieve and maintain such temperature conditions. The heating and cooling elements may comprise any of the temperature control equipment and/or methods described in relation to stage(s) 1002 but configured to control temperature conditions of other portions of interaction chamber 1000 or of interaction chamber 1000 at large.

Interaction chamber 1000 may include one or more detectors 1020. Detectors 1020 may be configured to measure conditions associated with interaction chamber 1000. In some embodiments, measurements may be taken on a single-shot basis. That is, detectors 1020 may be configured to measure properties associated with an individual interaction between electromagnetic radiation beam 316 and ion-generating target 304. Detectors 1020 may also measure the same or different properties on a more continuous basis, for example, providing results after processing.

Placement of detectors 1020 may vary based on a number of factors, including space constraints and optimal location for measurement. As shown in FIG. 10, detectors 1020 may be located along an outer wall of interaction chamber 1000 (such as detector 1020a), proximate to ion-generating target 304 (such as detectors 1020b and 1020c), or in line with proton beam 318 (such as 1020d).

For some detectors 1020, there may be an advantage to detection proximate to ion-generating target 304, and thus to interaction between electromagnetic radiation beam 316 and ion-generating target 304 (laser-target interaction). In an embodiment, system 300 may be stabilized over time, after which such proximity may be unnecessary. In some embodiments, one or more detectors 1020 may be mounted outside of interaction chamber 1000. For example, FIG. 10 depicts detector 1020e outside interaction chamber 1000 proximate to window 1018. Detectors 1020 may be disposed such that they are inherently subject to properties intended to be measured or conditions within interaction chamber 1000 may be altered to facilitate measurement. For example, optics component(s) 1006 may include a steering mirror configured to temporarily or intermittently deflect a signal from an interaction area to a detector, such as detector 1020e through window 1018. The above detector placements are merely exemplary, and numerous others may be apparent to those of skill in the art.

In some embodiments, one or more detectors 1020 may be configured to measure one or more laser-target interaction properties of electromagnetic radiation beam 316 or proton beam 318. In some embodiments, detectors 1020 may include quadrupole analyzers, spherical mirror analyzers ("SMAs"), cylindrical mirror analyzers ("CMAs"), secondary electron detectors, photomultipliers, scintillators, solid-state detectors, time-of-flight detectors, laser-on-target optical diagnostic detectors, x-ray detectors, cameras, Faraday cups, or other detectors. Detectors 1020 may detect properties such as absorption or reflection, a secondary electron emission property, a plasma property such as electron temperature and/or density, and/or an x-ray emission property. Secondary emissions, such as emission of electrons and/or x-rays may be indicative of laser-target interaction properties and/or properties of proton beam 318. For example the energy spectrum and/or flux of electrons and/or x-rays may indicate proton beam properties. These signals may then be used as input in a feedback loop for modifying the laser-target interaction, for example, by adjusting one or more of electromagnetic radiation source 302, optics component(s) 306, proton beam adjustment component(s) 308, and the position/orientation of ion-generating target 304, as described in greater detail below.

Detectors 1020 may be configured to detect proton beam direction, spatial spread, intensity, flux, energy, proton energy, and/or energy spread. For example, in some embodiments, a Thompson parabola may be employed. In such embodiments, proton beam 318 may be directed into an area in which magnetic and electric fields deflect the protons to locations on a detection screen. The location at which the protons contact the screen may indicate proton energy. For such a screen, any proton sensitive device may be used, such as CR-39 plates, image plates, and/or scintillators (coupled to a imaging device such as a CCD camera). As another example spatial proton beam distribution may be detected with a screen sensitive to protons, such as CR-39 and image plate or a scintillator with a detection device (such as a camera) may be used.

Detectors 1020 may also include a time-of-flight detector. The time of flight detector may measure average proton energy. In some embodiments, the time of flight detector may include a proton scintillator and a detector with adequate temporal resolution, such as a photo-multiplier tube (PMT). The time when the proton signature is detected on the PMT may indicate proton velocity and thus proton energy.

Detectors 1020 may also include instruments configured for plasma diagnostics, such as x-ray spectrometers configured to detect electron temperature and density, or interferometers configured to detect plasma density. Optical diagnostics may include imaging of the reflected laser beam to measure the laser absorption efficiency. These detectors may be used during initial system design, calibration, and testing, and they may optionally be included in the final system.

Referring back to FIG. 9, in step 906 interaction of an electromagnetic radiation beam (e.g., 316) with ion-generating target (e.g., 304) may generate particles, including protons. In some embodiments, the surface of ion-generating target 304 may be scanned by electromagnetic radiation beam 316. For example, the electromagnetic beam 316 may be sequentially scanned over the surface of ion-generating target 304 by continuous or discontinuous rastering, stepwise scanning, or any other scanning waveform desired. Alternatively, the electromagnetic beam 316 may be non-sequentially scanned over the surface of ion-generating target 304. Electromagnetic radiation beam scanning may be achieved by manually or automatically adjusting one or more optics component(s) 306 located between electromagnetic radiation source 302 and ion-generating target 304. Automatic adjustment of optics component(s) 306 may be achieved, for example, in response to one or more signals provided by control system 314. The one or more control signals provided by control system 314 may be predetermined by a program, such as a program stored in computing system 500, or they may be provided in response to one or more feedback signals received from various elements of system 300, such as one or more detectors. For example, information from the one or more detectors in system 300 may indicate that altering the location of the laser-target interaction site is desirable. This and other examples of feedback are discussed in greater detail below.

In step 908, system 300 may form proton beam 318 from the particles and direct proton beam 318 to the treatment volume. Protons generated in step 906 may not initially be disposed in a useful configuration or trajectory. The protons may be formed into a proton beam, for example by one or more beam adjustment component(s) 308. Properties of the proton beam may vary based on the configuration of system 300 and from use to use. In an embodiment, the proton energies may be about 250 MeV, as noted above, and may range, for example, from 60 to 250 MeV. Proton flux may be about 2 Gy/min, and proton pulse duration may be less than 100 psec. Protons generated by system 300 may also have a symmetric phase space profile, allowing improvements in proton beam steering and filtering over accelerator-based proton generation systems, thereby improving the accuracy and the efficiency of proton beam delivery and treatments. Of course, the above ranges are only examples, and the specific energies and flux may vary based on particulars of the configuration.

In accordance with the present disclosure, feedback may be used to adjust one or more properties of a proton beam. As used in the present disclosure, feedback may refer to a control protocol in which one or more system output is routed back into the system (i.e., fed back into the system) as one or more input as part of a cause-and-effect chain. For example, a processor (as described above) may be configured to produce a feedback signal to control aspects of an electromagnetic radiation beam, a proton beam, and/or a laser-target interaction. Such a feedback signal may, for example, be based on one or more property of an electromagnetic radiation beam, a proton beam, and/or a laser-target interaction. In some embodiments, a feedback signal may alter a proton beam by adjusting at least one of an electromagnetic radiation source, one or more optics components, and/or a position or orientation of an electromagnetic radiation beam relative to an ion-generating target. Feedback may, in some instances, be used to determine a structure of an ion-generating target.

Feedback signals may be configured to alter aspects of an electromagnetic radiation beam. For example, a processor may generate one or more feedback signal configured to adjust an electromagnetic radiation source to alter a temporal profile of an electromagnetic radiation beam. Further, an electromagnetic radiation source may be configured to generate a main pulse and a pre-pulse of an electromagnetic radiation beam, and a processor may configured to cause the electromagnetic radiation source to alter a contrast ratio of the pre-pulse to the main pulse in response to a feedback signal.

Moreover, a processor may be configured to generate a feedback signal to alter an energy of an electromagnetic radiation beam or a spatial or temporal profile of an electromagnetic radiation beam. For example, one or more optics component(s) may alter a spot size of an electromagnetic radiation beam in response to a feedback signal. In some embodiments, a motor may alter a relative orientation between an electromagnetic radiation beam and an ion-generating target in response to a feedback signal. And in some embodiments, an adaptive mirror may direct an electromagnetic radiation beam at an ion-generating target in response to a feedback signal.

Figure 11:
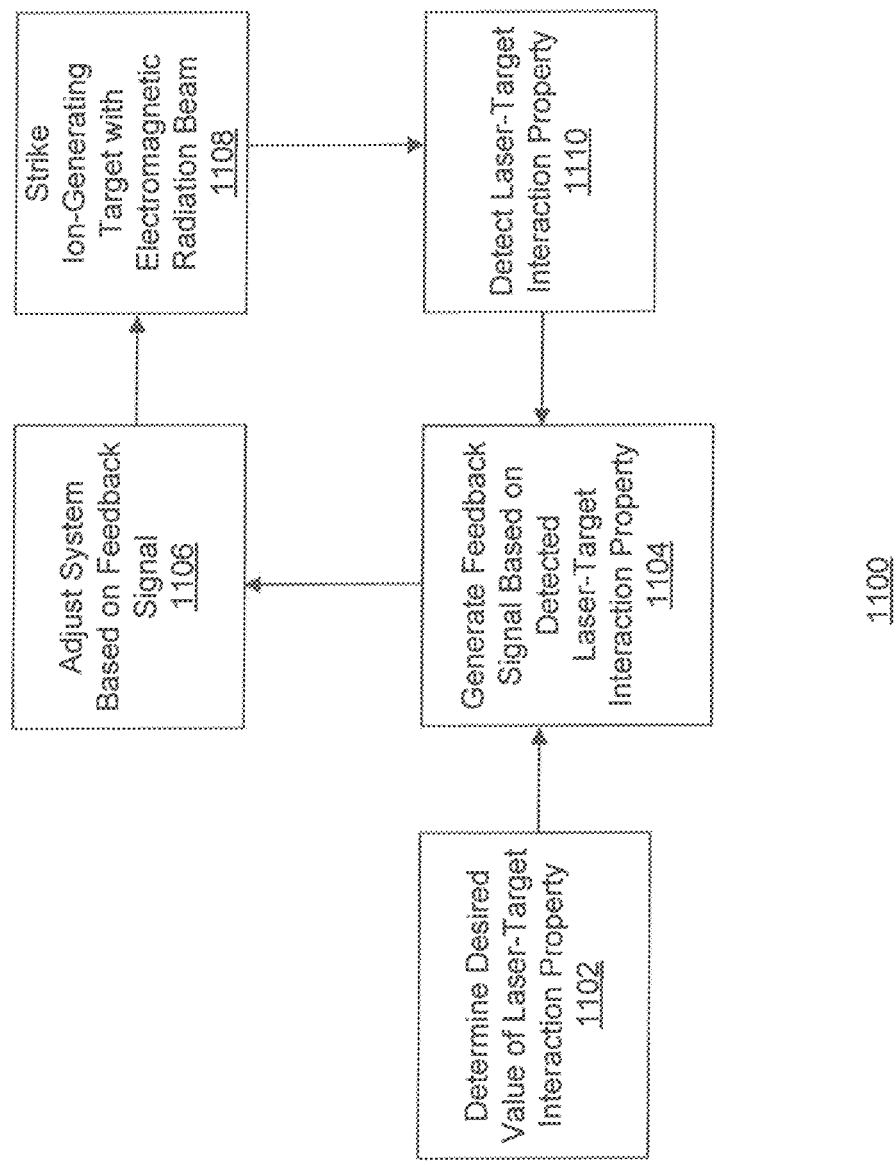
FIG. 11 is a flowchart of an example of a process for controlling proton therapy with proton generation feedback, consistent with disclosed embodiments.

In some embodiments, feedback may be used to adjust properties of proton beam 318. FIG. 11 depicts a process flow in an exemplary process 1100 for employing such feedback. At step 1102, system 300 may determine or be programmed with a desired value of a laser-target interaction property. The laser-target interaction property may be based on any of the properties detected by any of detectors 1020 described above. The desired value may be based, for example, on a nominal value related to a quality desired in proton beam 318, a value based on a desired property in a treatment plan, an optimal operating state of system 300, etc.

At step 1104, system 300 may generate one or more feedback signal(s) based on the detected laser-target interaction property. Feedback may be received and/or processed by control system 314. For example, control system 314 may calculate adjustments to various components of system 300 by comparing a laser-target interaction property to the desired value of the laser-target interaction property established at step 1102. In some embodiments, adjustment and comparison may be carried out according to a feedback control algorithm, such as a PID (proportioning-integrating-differentiating) control loop. The relationship(s) defined by the feedback signal(s) may be linear (e.g., an increase of pulse duration may affect proton energy inversely ($E_p \sim 1/t$)). The feedback signal may, at times (e.g., during startup or idle periods), be set to zero, set to an initial value indicating no adjustment is necessary, or set to a default value indicating an initial state.

At step 1106, system 300 may adjust one or more system components based on the feedback signal. For example, in some embodiments control system 314 may be configured to adjust a property of electromagnetic radiation beam 316 based on the feedback signal. The generated feedback may cause a motor to adjust a path of electromagnetic radiation beam 316. The motor may, for example adjust one or more of optics component(s) 306. Such adjustments may, for example, cause electromagnetic radiation beam 316 to strike ion-generating target 304 at a more desirable location or locations, thereby altering a property of proton beam 318 resulting from electromagnetic radiation beam 316 striking ion-generating target 304. Such adjustments may also cause electromagnetic radiation beam to sequentially strike a plurality of contiguous features of ion-generating target 304, such that the features are irradiated at a desired rate. Additionally, optics component(s) 306 may be configured to scan electromagnetic radiation beam 316 over a surface of ion-generating target 304. As another example, ion-generating target 304 may be manipulated by a motor based on the feedback signal to move ion-generating target 304 in any of six degrees of freedom.

In some embodiments, at step 1108, control system 314 may cause electromagnetic radiation source 302 to alter an energy, wavelength, or temporal or spatial profile of electromagnetic radiation beam 316 in response to the feedback signal. Control system 314 may also cause electromagnetic radiation source 302 to alter a contrast ratio of a pre-pulse to a main pulse in response to the feedback signal. Such adjustments to electromagnetic radiation beam 316 via electromagnetic radiation source 302 may be achieved, for example, by adjusting one or more of the oscillator(s) 602, pump source(s) 604, optics 606, stretcher(s) 610, amplifier(s) 612, and compressor(s) 614 via controller(s) 616. In some embodiments, any optical element or other component of electromagnetic radiation source 302 or optics component(s) 306 may be changed, moved, oriented, or otherwise configured based on the feedback signal, resulting in any number of changes. The examples above are not intended to be limiting.

At step 1108, system 300 may direct electromagnetic radiation beam 316 to strike ion-generating target 304, for example as described above in relation to steps 902 and 904 of process 900, shown in FIG. 9.

At step 1110, system 300 may detect a laser-target interaction property. The detected laser-target interaction property may include any one or more of the properties described above in relation to detectors 1020 and/or any property detected in relation to electromagnetic radiation beam 316, proton beam 318, the laser-target interaction, fault conditions, or any other signal generated by any component of the system.

The laser-target interaction property detected at step 1110 may be passed back to step 1104, and process 1100 may repeat any number of times. For example, process 1100 may repeat a standard, fixed number of times, a number of times preset by control system 314, a number of times defined by a treatment plan, or a variable number of times determined in real-time.

In some embodiments, selection of protons of a particular energy and/or flux may be desired. For example, as described above with respect to the advantages of proton therapy, treatment of a treatment volume of a particular depth within a patient may be desired. Treatment depth may be specified by selectively emitting protons of a particular energy level or range of energy levels. The dose of radiation delivered to the treatment volume depends in part of the flux of the proton beam. Accordingly, it may be desirable to adjust the proton flux and proton energy produced by system 300.

In accordance with the present disclosure, a system for directing a pulsed beam of charged particles may include an ion source. As used in the present disclosure, an ion source may refer to any structure or device configured to produce a continuous or pulsed ion beam. A pulsed ion beam may refer to any group of ions that includes at least one ion bunch (e.g., a cluster of ions). In some embodiments, an ion source may include at least a radiation beam and an ion-generating target as described above; however, this example is not limiting. For example, a system for directing a pulsed beam of charged particles consistent with the present disclosures may be used with any beam of charged particles generated by any method or device (including, for example, a cyclotron, synchrotron, or other particle accelerator).

Further, in accordance with the present disclosure, a system for directing a pulsed beam of charged particles may include at least one electromagnet. As used herein, an electromagnet may refer to any device controllable to generate an electromagnetic field. In some embodiments, the at least one electromagnet may include a plurality of electromagnets in series along a trajectory of a pulsed ion beam.

Further, consistent with the present disclosure, a system for directing a pulsed beam of charged particles may include at least a zone proximate an electromagnet. As used in the present disclosure, a zone proximate to an electromagnet may refer to any location in which an electromagnetic field generated by the electromagnet is capable of altering the trajectory of a charged particle located within the zone. For example, a zone proximate to an electromagnet may include any location oriented such that an ion beam may traverse therethrough. In some embodiments, the zone may include a location within an electromagnetic field created by activation of an electromagnet. The size of the zone may vary depending on a number of factors; however, in some embodiments, the zone may have a dimension smaller than about one inch.

In accordance with the present disclosure, a system for directing a pulsed beam of charged particles may include at least one automated switch. As used in the present disclosure, an automated switch may refer to a device configured to be electrically connected to an electromagnet and configured to selectively activate or deactivate the at least one electromagnet when triggered by a signal. An automated switch may be any switch that may be selectively activated or deactivated. For example, the automated switch may include a photoconductive semiconductor switch or a spark switch. In some embodiments, the at least one automated switch may include a plurality of automated switches. Individual automated switches may be associated with different electromagnets or with the same electromagnet. In some embodiments, a first electromagnet may be configured to divert a portion of a pulsed ion beam from an original trajectory to a diverted trajectory. Some embodiments may further include a second electromagnet in series with the first electromagnet and configured to re-divert at least part of the diverted portion of the pulsed ion beam from the diverted trajectory to a path substantially parallel to the original trajectory.

In accordance with the present disclosure, a system for directing a pulsed beam of charged particles may include a radiation trigger source. As used in the present disclosure, a radiation trigger source may include any structure capable of producing radiation trigger to activate or deactivate at least one automated switch. For example a radiation trigger source may include one or more of an ion source, an x-ray source, an electron source, and a light source (e.g., a laser). In some embodiments, a radiation trigger produced by a radiation trigger source may be configured to activate or deactivate an automated switch and to irradiate an ion-generating target to thereby generate the pulsed ion beam.

In accordance with the present disclosure, at least one processor may be configured to activate least one electromagnet as an ion bunch traverses a zone proximate to the electromagnet. The at least one processor may include any of the processors described above and may be configured to activate a plurality of automated switches in sequence as the ion bunch traverses a series of electromagnets.

In accordance with the present disclosure, a controlled delay line may be provided. As used in the present disclosure, a controlled delay line may refer to a pathway configured to extend the time it takes for a beam of radiation or charged particles to traverse it. For example, a controlled delay line may be used to delay the time at which an ion bunch traverses a zone proximate to an electromagnet. As another example, a controlled delay line may be used to delay the time at which a radiation beam activates an automated switch. In some embodiments the controlled delay line may be configured to synchronize the time at which the radiation beam activates an automated switch of an electromagnet with the time at which a pulsed ion beam traverses a zone proximate to the electromagnet.

Figure 12:
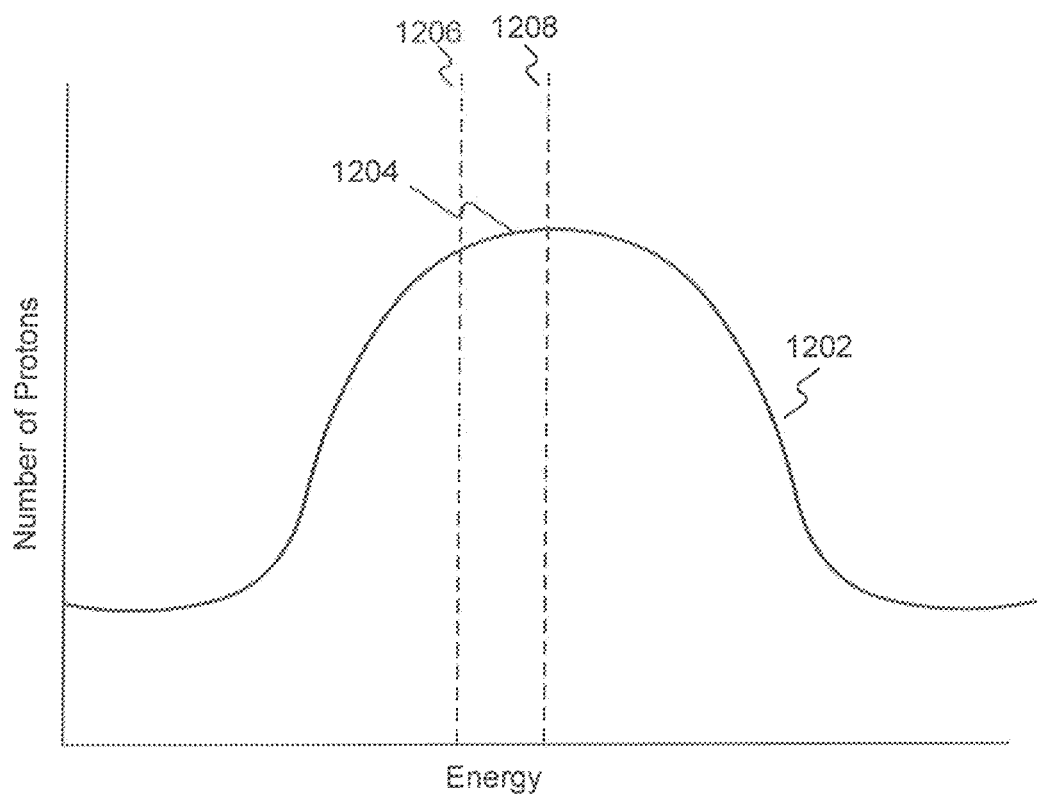
FIG. 12 depicts energy of an exemplary proton beam pulse consistent with disclosed embodiments.

FIG. 12 is an exemplary graph of a proton energy profile for an ion bunch, for example a proton bunch within proton beam 318. Pulse (i.e., "bunch") 1202, shown in FIG. 12, may be generated as described above in relation to system 300 and ion-generating target 304. Use of ion-generating target 304, however, is merely an example, and is not intended to be limiting. Other ion sources and type of ions may also be used.

In the context of proton therapy, to irradiate a treatment volume located at a particular depth within a patient, protons of certain energies may be desired. To isolate protons of the desired energies, system 300 may filter proton beam 318 to deliver protons having the desired energies to the patient, eliminating protons having other energies from the proton beam. For example, to deliver protons 1204 having energies between energy 1206 and energy 1208, system 300 may filter proton bunch 1202 by removing any protons having energies less than energy 1206 and greater than energy 1208.

Such filtering may be achieved by combining certain proton beam adjustment components 308. For example, proton beam adjustment components 308 may manipulate proton beam 318 such that protons having certain energies are diverted along a different trajectory than protons having other energies. This may be achieved in a number of ways. For example, proton beam adjustment components 308 may be configured as a band pass filter to isolate protons having energies between energy 1206 and energy 1208. In another embodiment, proton beam adjustment components 308 may be configured as a high pass filter to isolate protons having energies greater than an energy cut-off, such as energy 1206 or 1208. In another embodiment, proton beam adjustment components 308 may be configured as a low pass filter to isolate protons having energies less than an energy cut-off, such as energy 1206 or 1208.

The above embodiments may be combined, and more than one filter may be used. A low pass filter and a high pass filter may be combined in series, for example, to create a band pass filter. In such an embodiment, the low pass filter may be configured to isolate protons having energies less than energy 1208, and the high pass filter may be configured to isolate protons having energies greater than energy 1206. This may be particularly advantageous for selecting protons within a narrow energy band, especially an energy band narrower than a stand-alone band pass filter can accommodate.

To achieve proton energy filtering, one or more of proton beam adjustment components 308 may be selectively activated and/or controlled by one or more automated switches, such as a spark switch or photoconductive switch. Selective activation may be governed by controller 314, which may have interfaces with the automated switch and the proton beam adjustment components 308. The automated switch may be activated or deactivated by a signal generated by controller 314. The signal may be generated based on feedback, such as any of the forms of feedback described above.

Additionally or alternatively, in some embodiments the automated switch may be configured for activation or deactivation by electromagnetic radiation, such as a laser or another light source. For example, the automated switch may comprise a photoconductive semiconductor switch disposed along a path of electromagnetic radiation beam 316. Alternatively, electromagnetic radiation beam 316 may be diverted by one or more of optics components 306 or split into a plurality of beams by optics components 306, one or more of the plurality of beams being delivered to the automated switch. In such embodiments, the automated switch may be activated or deactivated when struck by electromagnetic radiation beam 316. Thus, electromagnetic radiation beam may be configured both to activate the automated switch and to irradiate ion-generating target 304 to generate the proton beam 318.

In other embodiments, a switching electromagnetic radiation source may not be associated with electromagnetic radiation source 302 or electromagnetic radiation beam 316. For example, control system 314 may cause a separate switching electromagnetic radiation source to irradiate one or more photoconductive semiconductor switch or spark switch, thereby activating or deactivating the proton beam adjustment components 308 of the proton energy filter(s).

Timing associated with activating the automated switch in a proton energy filter may be influenced, at least in part, by a time-of-flight control unit, such as a controlled delay line configured to adjust a time at which the radiation beam activates the automated switch. For example the controlled delay line may be configured to synchronize timing of the automated switch with the radiation beam. Additionally, or in the alternative, the timing associated with activating the automated switch in a proton energy filter may be controlled by control system 314, for example in response to a user command, a feedback signal from system 300, or in accordance with a predetermined program.

Although the above discussion contemplates an application in which protons are filtered in a proton therapy system, a person of ordinary skill in the art would appreciate that these filtering systems and methods have broad applicability. For example, these methods and systems described in the context of filtering protons may also be used to filter any variety of other charged particles used in any variety of other systems and applications.

FIG. 13 depicts an example of a configuration of proton beam adjustment components 308 configured to achieve proton energy selection as described above. Such a configuration may include one or more proton beam adjustment components 1302 and 1306, and a beam dump 1304.

In some embodiments, beam adjustment components 1302 and 1306 may include a plurality of electromagnets disposed in series along a trajectory of proton beam 318. A plurality of automated switches may be associated with one or more different magnets or groups of magnets. Control system 314 may be configured to activate such a plurality a switches in various combinations to manipulate proton beam 318. For example, control system 314 may activate the automated switches in sequence as a proton bunch traverses magnets of the plurality of electromagnets. In an embodiment, beam adjustment component 1302 may be configured to divert a portion of proton beam 318 from an original trajectory to a diverted trajectory. Beam adjustment component 1302 may be configured to redivert at least part of the diverted portion of the pulsed proton beam from the diverted trajectory to a path substantially parallel to the original trajectory.

Figure 13A:
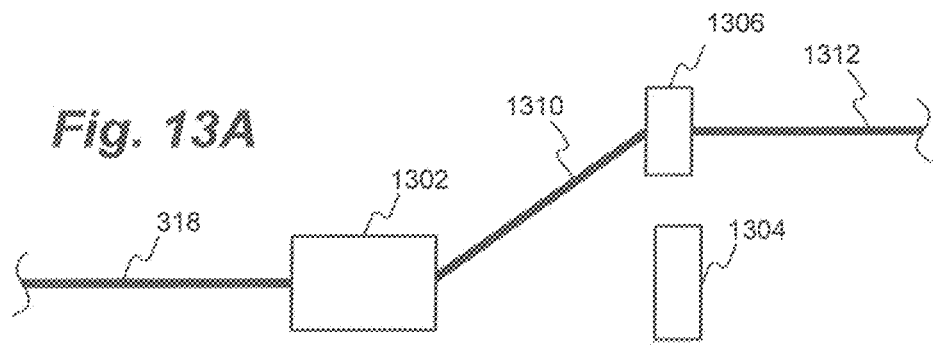
FIGS. 13A and 13B depict an example of a proton energy selection system, consistent with disclosed embodiments.
Figure 13B:
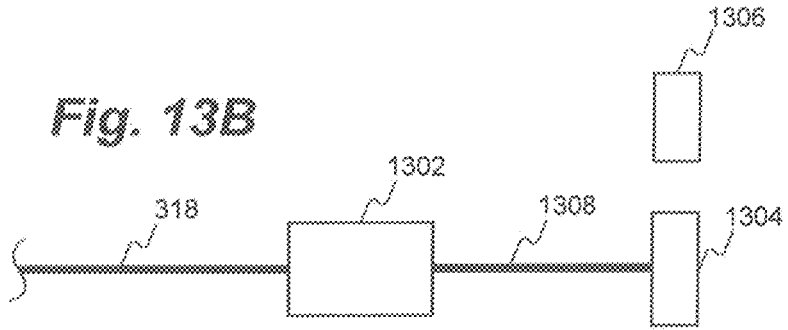

As shown in FIG. 13, proton beam 318 may pass through a zone proximate to proton beam adjustment component 1302. The zone may be of any size, but in some embodiments may have a dimension of less than one inch. The zone proximate to proton beam adjustment component 1302 may be configured and/or oriented for a proton beam 318 (e.g., a continuous beam or a pulsed beam including pulses such as pulse 1202) to traverse the zone. Proton beam adjustment component 1302 may include any of proton beam adjustment components 308, for example, an electromagnet such as a dipole, CMA, SMA, or time-of flight analyzer. As the proton beam traverses the zone proximate to proton beam adjustment component 1302, the automated switch may activate proton beam adjustment component 1302 such that protons having the desired energy are diverted along a trajectory 1310 toward beam adjustment component 1306, as shown in FIG. 13A. As protons having energies to be filtered out of proton beam 318 traverse the zone proximate to proton beam adjustment component 1302, the automated switch may not be activated, or an alternative switch may be activated, and the protons may travel along trajectory 1308 toward beam dump 1304, as shown in FIG. 13B. Protons having the desired energy may pass beam adjustment component 1306, where they are redirected back along a beam line trajectory 1312 and eventually toward the treatment volume.

In some embodiments (not shown), a proton energy filter may include only a single beam adjustment component and a beam dump. Instead of diverting protons having the desired energy towards a second electromagnetic element, protons having the desired energy may be allowed to pass through the zone proximate to proton beam adjustment component without being diverted. As protons having energies to be filtered out of the proton beam pass through the zone proximate to proton beam adjustment component, they may be diverted along a trajectory towards the beam dump.

In some embodiments, a proton energy filter may include an energy degrader. For example, an energy degrader may be used as part of beam dump 1304. Additionally, an energy degrader may be used to reduce energy and/or flux of the protons that are not diverted to the beam dump. To filter proton beam using an energy degrader, protons may be diverted through the degrader, where they interact with the degrader. Protons transmitted through the degrader along the trajectory of the proton beam then have reduced energies, thereby lowering the energy of the proton beam. Other protons may either be absorbed by the energy degrader or diverted from the trajectory of the proton beam, no longer forming part of the transmitted proton beam and thereby reducing the flux of the transmitted proton beam. An energy degrader may include, for example, carbon, plastics, beryllium, metals such as copper or lead, or any material that is effective at reducing the energy or flux of the proton beam. An energy degrader may also consist of any shape effective at reducing the energy or flux of the proton beam, including a wedge, a double wedge separated by a gap (which may be filled with air or another material), a cylinder, a rectangle, or any other material or configuration capable of degrading the beam.

Those having ordinary skill in the art will recognize that the proton beam filter configurations described above are only illustrative, and that other configurations are contemplated consistent embodiments described herein.

In accordance with the present disclosure, a system for treating a treatment volume with protons may include a proton source. As used in the present disclosure, a proton source may refer to any material, system or subsystem that has releasable protons or that is capable of releasing protons. A proton source may be configured to provide a proton beam having a plurality of proton energies within a proton energy spread.

Further, in accordance with the present disclosure, a system for treating a treatment volume with protons may include at least one processor configured to control a relative movement between a proton beam and a treatment volume in two dimensions of a three-dimensional coordinate system. The at least one processor may, for example, include any of the processors described above. In some embodiments, a processor may be configured to control a proton energy spread to adjust a depth of the treatment volume in the third dimension of the three-dimensional coordinate system while maintaining substantially fixed coordinates in the other two dimensions. For example, a third dimension of a three-dimensional coordinate system may refer to an approximate direction of a proton beam trajectory, and the other two dimensions refer to the plane orthogonal to the third dimension.

Controlling a relative movement between a proton beam and a treatment volume in two dimensions of a three-dimensional coordinate system may be achieved in numerous ways. For example controlling relative movement between the proton beam and the treatment volume may be achieved by rotating a gantry. Alternatively or additionally, controlling relative movement between the proton beam and a treatment volume may be achieved by directing a proton beam with an electromagnet and/or moving a patient support platform.

Likewise, controlling an energy spread and distribution or protons may be achieved in a variety of ways. In accordance with the present disclosure, controlling energy spread may be achieved, for example, via one or more of a magnetic analyzer, a time-of-flight control unit, and an energy degrader.

System 300 may be configured to vary of one or more properties of proton beam 318 as others remain substantially fixed. In some embodiments, such variation may be achieved via feedback, such as described above in relation to process 1100. For example, control system 314 may hold a flux of proton beam 318 substantially constant while independently adjusting an energy of proton beam 318, or hold the energy of proton beam 318 substantially constant while independently adjusting its flux. Such independent adjustment may not be feasible in accelerator-based systems because of their large sizes and slow response times. The systems and methods disclosed herein, however, may achieve independent energy and flux control by coupling feedback (as described above) with the adjustable components of system 300 (also described above) to reconfigure properties of electromagnetic radiation beam 316 and the laser-target interaction, thereby adjusting the energy and flux of proton beam 318 separately. Thus, precise treatment may be delivered more quickly than traditional systems, reducing time spent by patients in treatment and increasing patient throughput. Further, treatments can be provided more accurately and with less damage to healthy tissue. As an alternative, the systems and methods disclosed herein may achieve simultaneous energy and flux control by coupling feedback (as described above) with the adjustable components of system 300 (also described above) to reconfigure properties of electromagnetic radiation beam 316 and the laser-target interaction, thereby adjusting the energy and flux of proton beam 318 together.

In an embodiment, the energy and flux of proton beam 318 may be adjusted according to the intensity of electromagnetic radiation beam 316, the location of electromagnetic radiation beam on ion-generating target 304, the temporal profile of electromagnetic radiation beam 316, the spatial profile of radiation beam 316, the settings and choice of proton beam adjustment component(s) 308. As an example, the energy of proton beam 318 may be proportional to the intensity of electromagnetic radiation beam 316, and the flux of proton beam 318 may be proportional to the energy of electromagnetic radiation beam 316. This can be expressed by the following relationships:

$$E_p \sim I_L = \frac{E_L}{\Delta \tau \cdot A} \quad (1)$$

and $$\emptyset_p \sim E_L \quad (2)$$

in which $I_L$ is the intensity of electromagnetic radiation beam 316, $E_L$ is the intensity of electromagnetic radiation beam 316, A represents the spatial profile (e.g., a spot size) of electromagnetic radiation beam 316, $\Delta \tau$ represents the temporal profile (e.g., pulse duration) of electromagnetic radiation beam 316, $E_p$ is the energy of proton beam 318, and $\emptyset_p$ is the flux of proton beam 318. Accordingly, the energy of proton beam 318 may be held substantially constant while the flux of proton beam 318 varies, and vice versa, by properly adjusting one or more of the energy, spatial profile, and temporal profile of electromagnetic radiation beam 316. For example, to alter proton energy of proton beam 318 without changing proton flux, the energy of electromagnetic radiation beam 316 may be held constant at about 1 MeV while changing pulse duration and/or spot size at ion-generating target 304.

Alternatively or additionally, the energy and flux of proton beam 318 may be independently varied, for example, by choosing or adjusting proton beam adjustment component(s) 308 as appropriate. For example, this may be achieved by using one of the filtering systems and methods described above with respect to FIG. 13 or by using one or more energy degraders, for example.

When independently adjusting the flux of proton beam 318, the usable variation in the energy of proton beam 318 may be as large as ±25% or more where proton beam 318 is initially formed, and system 300 may be capable of reducing such fluctuations to about ±5% or less further down the beam line. Similarly, when independently adjusting the energy of proton beam 318, the usable variation in the flux of proton beam 318 may be as large as ±25% or more where proton beam 318 is initially formed, and system 300 may be capable of reducing such fluctuations to about ±5% or less further down the beam line.

As an alternative to independently adjusting the energy and flux of proton beam 318, the energy and flux of proton beam 318 may be simultaneously varied, for example, by choosing or adjusting proton beam adjustment component(s) 308 as appropriate. For example, this may be achieved by using one of the filtering systems and methods described above with respect to FIG. 13 or by using one or more energy degraders, for example.

Because process variables may fluctuate during operation, independent variance of the energy and flux of proton beam 318 benefits significantly from the feedback adjustments described above with respect to FIG. 11. For example, as the detected laser-target interaction property varies in step 1108 during operation, control system 314 may automatically adjusts system 300 accordingly at step 1104 via feedback signals determined at step 1110.

Figure 14:
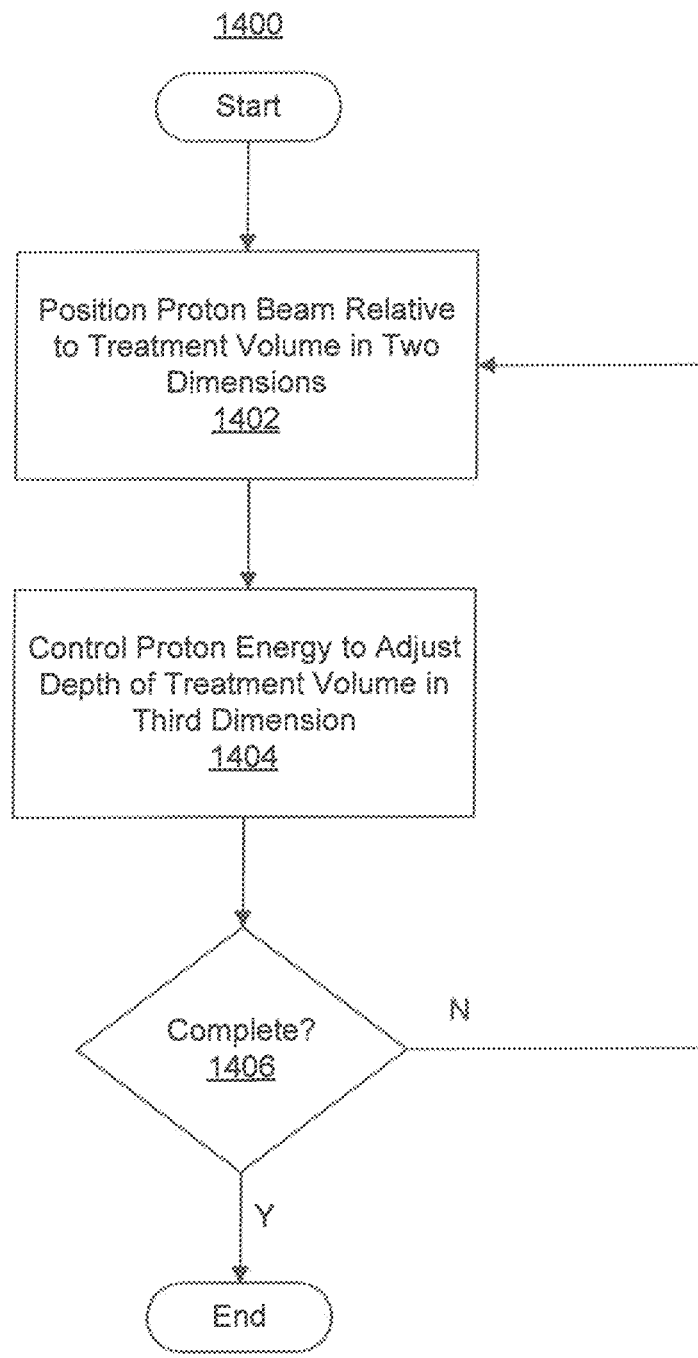
FIG. 14 is a flowchart of an example of a process for controlling proton therapy treatment in a three dimensional space, based on proton generation feedback, consistent with disclosed embodiments.

System 300 may be configured to employ such variation of one or more properties of proton beam 318 while holding other properties of proton beam 318 fixed in a process for systematic treatment of a treatment volume. FIG. 14 depicts an example of a process 1400 for such systematic treatment. At step 1402, control system 314 may position proton beam (e.g., beam 318) relative to the treatment volume in two dimensions of a three dimensional coordinate system. For example, the third dimension may be defined by the trajectory of the proton beam as it exits a gantry (e.g., gantry 310), and the two dimensions of the three dimensional coordinate system may be defined by the plane normal to the trajectory of proton beam 318 as it exits gantry 310. Relative movement between proton beam 318 and the treatment volume in the two dimensions may be controlled by one or more components of system 300. For example, relative movement may be controlled by any combination of one or more motors and/or magnets associated with gantry 310 and/or one or more motors associated with patient support platform 312. More specifically, control system 314 may be configured to control relative movement between proton beam 318 and a treatment volume by controlling one or more of a rotation of gantry 310, an adjustment of scanning magnets 710, and a repositioning of patient support platform 312.

At step 1404, control system (e.g., system 314) may be configured to control a relative movement between the proton beam and the treatment volume in a third dimension of the three-dimensional coordinate system. Control system 314 may be configured to control such relative movement in the third dimension while maintaining substantially fixed coordinates in the other two dimensions. For example, control system 314 may control proton energies to adjust a depth of the treatment while leaving the position of proton beam 318 in the other two dimensions fixed. Controlling the proton energies at step 1404 may be achieved via one or more of the techniques described above (with or without reference to the particular structure described above). For example, at least one of the energy, temporal profile, and spatial profile of electromagnetic radiation beam 316 may be adjusted in accordance with equation 1 above, a proton energy selection as in FIGS. 12 and 13 may be used, and/or one or more of a magnetic analyzer, a time-of-flight control unit, and an energy degrader may be used.

Figure 15A:
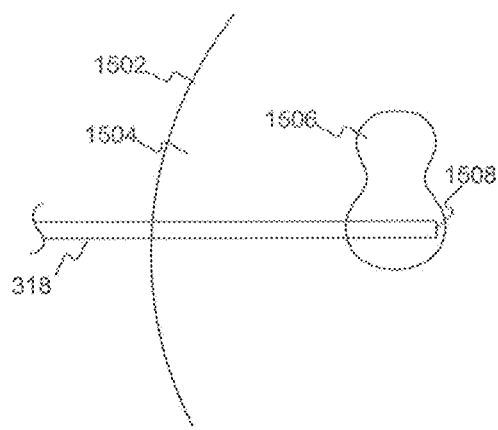
FIGS. 15A, 15B, 15C, and 15D depict aspects of an exemplary proton therapy treatment based on the process of FIG. 14.
Figure 15B:
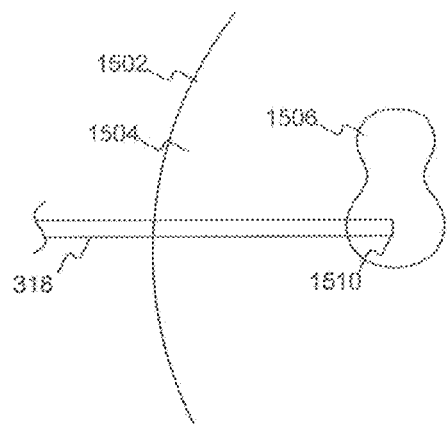
Figure 15C:
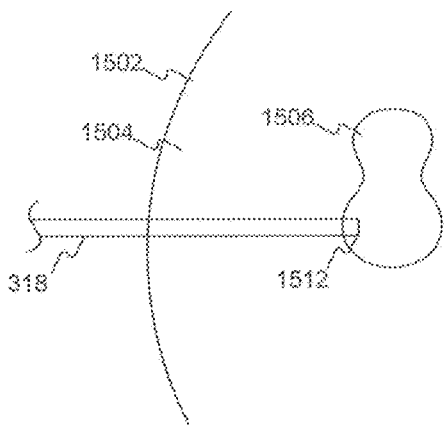

An example of step 1404 is shown in FIGS. 15A, 15B, and 15C, which depict proton beam 318 penetrating skin 1502 of a patient 1504, to provide treatment to a treatment volume 1506. FIGS. 15A, 15B, and 15C may represent a sequence of locations of treatment consistent with the disclosed embodiments. System 300 may be configured to treat an area 1508, shown in FIG. 15A, of a greater distance in the third dimension (i.e. further from patient 1504's skin 1502) before treating an area 1510 by reducing the energy of proton beam 318, as shown in FIG. 15B, and then treating an area 1512, shown in FIG. 15C, by further reducing the energy of proton beam 318. Alternatively, the sequence may be reversed, treating area 1512 of FIG. 15C, then increasing the energy of proton beam 318 to treat area 1510 of FIG. 15B, then further increasing the energy of proton beam 318 to treat area 1508 of FIG. 15A.

Additional locations of treatment may be included at step 1404 before, after, or intermediate to the areas 1508, 1510, and 1512 shown in FIGS. 15A, 15B, and 15C. Control system 314 may also be configured to optimize treatment to take into account effects of a particular sequence. For example, protons passing through treatment volume 1506 that are intended to treat area 1508 (i.e., as shown in FIG. 15A) may provide some collateral treatment to areas 1510 and 1512 before reaching 1508. Control system 314 may account for collateral doses administered to areas 1510 and 1512 by adjusting dosages in a patient's treatment plan accordingly. For example, control system 314 may be configured to integrate all of the collateral doses that will be delivered to areas 1510 and 1512 while directly treating other areas, such as area 1508, and to subtract those collateral doses from the direct dose appropriate to treat areas 1510 and 1512. Thus, a more accurate treatment can be achieved.

Figure 15D:
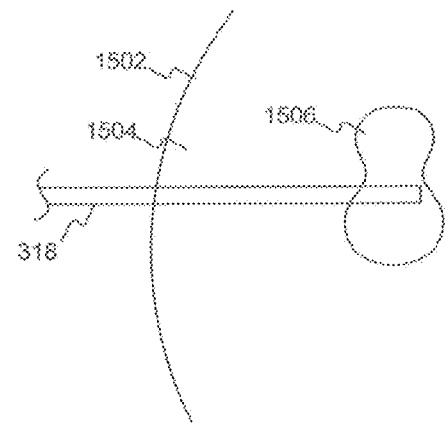

At step 1406, a control system (e.g., control system 314) may determine whether another position requires treatment or whether treatment is complete. If treatment is complete (step 1006; YES), process 1400 may end. If treatment is not complete (step 1006; NO), process 1000 may return to step 1002, repositioning proton beam 318 relative to the two dimensions, as shown in FIG. 15D, and repeating the process of scanning the depth in the third dimension by varying the energy of proton beam 318.

While illustrative embodiments have been described herein, the scope thereof includes any and all embodiments having equivalent elements, modifications, omissions, combinations (e.g., of aspects across various embodiments), adaptations and/or alterations as would be appreciated by those in the art based on the present disclosure. For example, the number and orientation of components shown in the exemplary systems may be modified. Further, with respect to the exemplary methods illustrated in the attached drawings, the order and sequence of steps may be modified, and steps may be added or deleted.

Aspects of the invention may include a system for generating a proton beam, the system comprising an interaction chamber configured to support an ion-generating target; an electromagnetic radiation source configured to provide an electromagnetic radiation beam; one or more optics components configured to direct the electromagnetic radiation beam at the ion-generating target to thereby cause a resultant proton beam; a detector configured to measure at least one laser-target interaction property; and one or more processors configured to produce a feedback signal based on the at least one laser-target interaction property measured by the detector and to alter the proton beam by adjusting at least one of the electromagnetic radiation source, the one or more optics component, and at least one of a relative position and orientation of the electromagnetic radiation beam to the ion-generating target.

The laser-target interaction property may include a proton beam property, such as, for example, a proton beam energy and/or a proton beam flux, which may include a secondary electron emission property. As another example, the laser-target interaction property may include an x-ray emission property.

The electromagnetic radiation source may be configured to provide a pulsed electromagnetic radiation beam and to thereby cause a pulsed proton beam.

The interaction chamber may include a target stage for supporting the ion-generating target, and the one or more processors may be further configured to cause relative movement between the target stage and the electromagnetic radiation beam.

The structure of the ion-generating target may be determined, at least in part, based upon a generated feedback signal generated from a measured laser-target interaction property.

The laser-target interaction property may include a proton beam energy and/or a proton beam flux.

In response to the feedback signal, the at least one processor may be configured to cause the electromagnetic radiation source to alter an energy of the electromagnetic radiation beam, a temporal profile of the electromagnetic radiation beam, and/or a spatial of the electromagnetic radiation beam (e.g., a spot size of the electromagnetic radiation beam).

In response to the feedback signal, the at least one processor may be configured to cause the one or more optics components to alter an energy of the electromagnetic radiation beam, a temporal profile of the electromagnetic radiation beam, and/or a spatial of the electromagnetic radiation beam (e.g., a spot size of the electromagnetic radiation beam).

The electromagnetic radiation source may be configured to alter a temporal profile of the electromagnetic radiation beam in response to the feedback signal, and/or may also be configured to generate at least a main pulse and a pre-pulse. The at least one processor may be configured to cause the electromagnetic radiation source to alter a contrast ratio of the pre-pulse to the main pulse in response to the feedback signal.

The at least one processor may be configured to cause a motor to alter the relative orientation between the electromagnetic radiation beam and the ion-generating target in response to the feedback signal.

Aspects of the invention may also include a system for generating a proton beam, the system comprising an interaction chamber configured to support an ion-generating target; an electromagnetic radiation source configured to provide an electromagnetic radiation beam; an adaptive mirror configured to direct the electromagnetic radiation beam at the ion-generating target in the interaction chamber to thereby generate a proton beam; and at least one processor configured to control the adaptive mirror so as to adjust at least one of a spatial profile of the electromagnetic radiation beam and at least one of a relative position and orientation between the electromagnetic radiation beam and the ion-generating target.

The adaptive mirror may be configured to direct the electromagnetic radiation beam by at least one of adjusting a focus of the electromagnetic radiation beam, diverting the electromagnetic radiation beam, and scanning the electromagnetic radiation beam. The adaptive mirror may also be configured to raster the electromagnetic radiation beam over the ion-generating target. The adaptive mirror may include a plurality of facets, each of the plurality of facets being independently controllable by digital logic circuitry. The adaptive mirror may include a laser pulse focused onto an anti-reflective coated substrate, one or both of the laser pulse and anti-reflective coated substrate being controllable by a digital logic circuitry.

The at least one processor may be configured to cause the adaptive mirror to direct the electromagnetic radiation beam at the ion-generating target in response to a feedback signal, and/or to cause the adaptive mirror to direct the electromagnetic radiation beam at predetermined locations on a surface of the ion-generating target. A surface of the ion-generating target may include a patterned array, and/or a plurality of ion-generating structures substantially oriented along a common axis. Alternatively or additionally, a surface of the ion-generating target may include one or more knife edges.

The specification and claims may refer to elements in the singular, such as "a processor" or "a detector." It is to be understood that this syntax is intended to be inclusive of multiple of such elements. That is, a particular function may be split over multiple processors located on a same board or system, or located remotely on another board or in another system. It is to be understood that reference to a processor is to be interpreted as "at least one processor," meaning that the function recited may occur across multiple processors and still be considered within the scope of the disclosure and claims. The same is true for detectors and other elements described or referenced in the singular throughout the specification and claims.

Moreover, the foregoing description has been presented for purposes of illustration. It is not exhaustive and is not limiting to the precise forms or embodiments disclosed. Modifications and adaptations will be apparent to those skilled in the art from consideration of the specification and practice of the disclosed embodiments. For example, where generation of protons is described above with respect to a laser striking an ion-generating target, other proton generation processes may be used, such as a radio-frequency coupling. Further, while some description above relates to use of protons in medicine as a radiotherapy treatment, systems and methods described herein may be used in other applications of a proton beam and in applications involving other ions than protons.

The claims are to be interpreted broadly based on the language employed in the claims and not limited to examples described in the present specification, which examples are to be construed as non-exclusive. Further, the steps of the disclosed methods may be modified in any manner, including by reordering steps and/or inserting or deleting steps.

The invention claimed is:

1. A system for generating a proton beam, the system comprising:
   an interaction chamber configured to support an ion-generating target;
   an electromagnetic radiation source configured to provide an electromagnetic radiation beam;
   one or more optics components configured to direct the electromagnetic radiation beam at the ion-generating target to thereby cause a resultant proton beam;
   a detector configured to measure at least one laser-target interaction property; and
   at least one processor configured to:
      receive a feedback signal based on the at least one laser-target interaction property measured by the detector, wherein the feedback signal is indicative of a relationship between the proton beam and the electromagnetic radiation beam; and
      based on the received feedback signal, alter the proton beam by adjusting an item among at least one of the following: (A) the electromagnetic radiation source, (B) the one or more optics components, (C) at least one of a relative position and orientation of the electromagnetic radiation beam to the ion-generating target;
wherein altering the proton beam includes altering a temporal profile of the electromagnetic radiation beam based on the relationship between the proton beam and the electromagnetic radiation beam as indicated in the received feedback signal and by altering a chirp of the electromagnetic radiation beam.

2. The system for generating a proton beam in claim 1, wherein the laser-target interaction property includes a proton beam property.

3. The system for generating a proton beam in claim 1, wherein the laser-target interaction property includes an x-ray emission property.

4. The system for generating a proton beam in claim 1, wherein the laser-target interaction property includes an energy spectrum of electromagnetic radiation.

5. The system for generating a proton beam in claim 1, wherein the interaction chamber includes a target stage for supporting the ion-generating target, and the at least one processor is further configured to cause relative movement between the target stage and the electromagnetic radiation beam.

6. The system for generating a proton beam in claim 2, wherein the proton beam property includes a proton beam energy.

7. The system for generating a proton beam in claim 2, wherein the proton beam property includes a proton beam flux.

8. The system for generating a proton beam in claim 1, wherein the electromagnetic radiation source is configured to generate a main pulse and a pre-pulse, and the at least one processor is configured to cause the electromagnetic radiation source to alter a contrast ratio of the pre-pulse to the main pulse based on the relationship between the proton beam and the electromagnetic radiation beam as indicated in the received feedback signal.

9. The system for generating a proton beam in claim 1, wherein the at least one processor is configured to cause the electromagnetic radiation source to alter an energy of the electromagnetic radiation beam based on the relationship between the proton beam and the electromagnetic radiation beam as indicated in the received feedback signal.

10. The system for generating a proton beam in claim 1, wherein the at least one processor is configured to cause the electromagnetic radiation source to alter a spatial profile of the electromagnetic radiation beam based on the relationship between the proton beam and the electromagnetic radiation beam as indicated in the received feedback signal.

11. The system for generating a proton beam in claim 1, wherein the at least one processor is configured to cause the one or more optics components to alter a spot size of the electromagnetic radiation beam based on the relationship between the proton beam and the electromagnetic radiation beam as indicated in the received feedback signal.

12. The system for generating a proton beam in claim 1, wherein the at least one processor is configured to cause a motor to alter the relative orientation between the electromagnetic radiation beam and the ion-generating target based on the relationship between the proton beam and the electromagnetic radiation beam as indicated in the received feedback signal.

13. The system for generating a proton beam in claim 1, wherein the at least one processor is configured to alter the temporal profile of the electromagnetic radiation beam by altering a timing of one or more laser pump sources.

14. The system for generating a proton beam in claim 1, wherein the electromagnetic radiation source is configured to generate a main pulse and a pre-pulse, and the at least one processor is configured control a timing of the pre-pulse based on the relationship between the proton beam and the electromagnetic radiation beam as indicated in the received feedback signal.

15. A system for generating a proton beam, the system comprising:
an interaction chamber configured to support an ion-generating target;
an electromagnetic radiation source configured to provide an electromagnetic radiation beam;
one or more optics components configured to direct the electromagnetic radiation beam at the ion-generating target to thereby cause a resultant proton beam;
a detector configured to measure at least one laser-target interaction property, wherein the laser-target interaction property includes a secondary electron emission property; and
at least one processor configured to:
receive a feedback signal based on the at least one laser-target interaction property measured by the detector, wherein the feedback signal is indicative of a relationship between the proton beam and the electromagnetic radiation beam; and
based on the received feedback signal, alter the proton beam by adjusting an item among at least one of the following: (A) the electromagnetic radiation source, (B) the one or more optics components, (C) at least one of a relative position and orientation of the electromagnetic radiation beam to the ion-generating target.

16. A method for generating a proton beam, the method comprising:
producing an electromagnetic radiation beam;
directing the electromagnetic radiation beam at an ion-generating target to thereby cause a resultant proton beam;
measuring at least one laser-target interaction property with a detector;
receiving a feedback signal based on the at least one laser-target interaction property measured by the detector, wherein the feedback signal is indicative of a relationship between the proton beam and the electromagnetic radiation beam; and
based on the received feedback signal, altering the proton beam by adjusting an item among at least one of the following: (A) the electromagnetic radiation source, (B) the one or more optics component, (C) at least one of a relative position and orientation of the electromagnetic radiation beam to the ion-generating target;
wherein altering the proton beam includes altering a temporal profile of the electromagnetic radiation beam based on the relationship between the proton beam and the electromagnetic radiation beam as indicated in the received feedback signal by altering a timing of one or more laser pump sources.

17. The method of claim 16, wherein measuring the at least one laser-target interaction property includes measuring a member of at least one of the following categories: (A) a proton beam property, (B) a secondary electron emission property, (C) an x-ray emission property, (D) an energy spectrum of electromagnetic radiation.

18. The method of claim 16, wherein altering the temporal profile of the electromagnetic radiation beam by is achieved by altering a chirp of the electromagnetic radiation beam.

* * * * *